United States Patent
Amble et al.

(10) Patent No.: US 9,021,358 B2
(45) Date of Patent: Apr. 28, 2015

(54) MULTI-SITE VIDEO BASED COMPUTER AIDED DIAGNOSTIC AND ANALYTICAL PLATFORM

(71) Applicant: EaglEyeMed, Santa Clara, CA (US)

(72) Inventors: Ravi Amble, San Jose, CA (US); Farooq Raza, Milpitas, CA (US)

(73) Assignee: EaglEyeMed, Inc., Santa Clara, CA (US)

( * ) Notice: Subject to any disclaimer, the term of this patent is extended or adjusted under 35 U.S.C. 154(b) by 0 days.

(21) Appl. No.: 14/214,321

(22) Filed: Mar. 14, 2014

(65) Prior Publication Data

US 2014/0282018 A1    Sep. 18, 2014

Related U.S. Application Data

(60) Provisional application No. 61/800,316, filed on Mar. 15, 2013.

(51) Int. Cl.
| | |
|---|---|
| G06F 3/00 | (2006.01) |
| A61B 5/00 | (2006.01) |
| A61B 8/00 | (2006.01) |
| G06F 3/048 | (2013.01) |
| G06Q 50/24 | (2012.01) |
| G01S 7/52 | (2006.01) |
| G06F 3/0481 | (2013.01) |
| H04L 29/06 | (2006.01) |

(52) U.S. Cl.
CPC ............. *G06Q 50/24* (2013.01); *G01S 7/52074* (2013.01); *G06F 3/0481* (2013.01); *H04L 29/06* (2013.01); *A61B 5/002* (2013.01)

(58) Field of Classification Search
CPC .................................................. G01S 7/52074
USPC .......................................... 600/440; 715/733
See application file for complete search history.

(56) References Cited

U.S. PATENT DOCUMENTS

| | | |
|---|---|---|
| 5,441,047 A | 8/1995 | David et al. |
| 5,553,609 A | 9/1996 | Chen et al. |
| 5,827,180 A | 10/1998 | Goodman |

(Continued)

OTHER PUBLICATIONS

Non-Final Office Action from U.S. Appl. No. 10/109,958 dated May 17, 2005.

(Continued)

*Primary Examiner* — Jennifer To
*Assistant Examiner* — Sunil Sundar
(74) *Attorney, Agent, or Firm* — Zilka-Kotab, PC

(57) ABSTRACT

In one embodiment, a method includes receiving a stream of biometric imaging data of a patient; receiving medical data about the patient; receiving a video stream depicting a source of the biometric imaging data; receiving supplemental information selected from a group consisting of: a second video stream depicting a human, one or more use cases corresponding to the biometric imaging data, an image of anatomy comparable to the biometric imaging data; and preparing for simultaneous output to a graphical user interface on a single display screen: the biometric imaging data, the medical data, the video stream depicting a source of the biometric imaging data, and the supplemental information. Each of the biometric imaging data, the medical data about the patient, the video stream depicting a source of the biometric imaging data, and the supplemental information is simultaneously output in a unique region of the graphical user interface.

6 Claims, 14 Drawing Sheets

(56) References Cited

U.S. PATENT DOCUMENTS

| | | | |
|---|---|---|---|
| 5,987,519 | A | 11/1999 | Peifer et al. |
| 6,083,248 | A | 7/2000 | Thompson |
| 6,364,834 | B1 | 4/2002 | Reuss et al. |
| 6,381,577 | B1 | 4/2002 | Brown |
| 6,424,996 | B1* | 7/2002 | Killcommons et al. ...... 709/206 |
| 6,442,432 | B2 | 8/2002 | Lee |
| 6,599,250 | B2 | 7/2003 | Webb et al. |
| 6,681,003 | B2 | 1/2004 | Linder et al. |
| 6,705,990 | B1* | 3/2004 | Gallant et al. ................ 600/300 |
| 6,738,798 | B1 | 5/2004 | Ploetz et al. |
| 6,804,656 | B1 | 10/2004 | Rosenfeld et al. |
| 6,820,057 | B1 | 11/2004 | Loch et al. |
| 7,038,588 | B2* | 5/2006 | Boone et al. ............... 340/573.1 |
| 7,188,151 | B2 | 3/2007 | Kumar et al. |
| 7,549,961 | B1* | 6/2009 | Hwang .......................... 600/440 |
| 8,005,691 | B2 | 8/2011 | Kumar et al. |
| 8,069,420 | B2 | 11/2011 | Plummer |
| 2001/0056226 | A1 | 12/2001 | Zodnik et al. |
| 2002/0198473 | A1 | 12/2002 | Kumar et al. |
| 2003/0046562 | A1 | 3/2003 | Uchikubo |
| 2004/0039606 | A1 | 2/2004 | Loch et al. |
| 2007/0130287 | A1 | 6/2007 | Kumar et al. |
| 2008/0146277 | A1* | 6/2008 | Anglin et al. ............... 455/556.1 |
| 2009/0125147 | A1* | 5/2009 | Wang et al. .................... 700/264 |
| 2009/0189988 | A1 | 7/2009 | Jia et al. |
| 2009/0192824 | A1* | 7/2009 | Minakuchi et al. ............... 705/3 |
| 2010/0325546 | A1 | 12/2010 | Leo et al. |
| 2011/0301461 | A1* | 12/2011 | Anite ............................ 600/443 |
| 2012/0179039 | A1* | 7/2012 | Pelissier et al. ............... 600/443 |
| 2012/0290976 | A1* | 11/2012 | Lahm et al. .................... 715/810 |

OTHER PUBLICATIONS

Non-Final Office Action from U.S. Appl. No. 10/109,958 dated Dec. 22, 2005.

Final Office Action from U.S. Appl. No. 10/109,958 dated Jul. 21, 2006.

Notice of Allowance and Fee(s) Due from U.S. Appl. No. 10/109,958 dated Nov. 9, 2006.

Supplemental Notice of Allowability from U.S. Appl. No. 10/109,958 dated Dec. 19, 2006.

Non-Final Office Action from U.S. Appl. No. 11/668,399 dated Aug. 20, 2009.

Final Office Action from U.S. Appl. No. 11/668,399 dated Nov. 15, 2010.

Notice of Allowance and Fee(s) Due from U.S. Appl. No. 11/668,399 dated Apr. 14, 2011.

International Preliminary Examination Report from PCT Application No. PCT/US02/09914 dated Feb. 12, 2003.

Conrad, E., "Advanced Encryption Standard (AES)," Published by Federal Information Processing Standard (FIPS), Publication 197, 1997, pp. 1-6.

International Search Report and Written Opinion from PCT Application No. PCT/US2014/029590 dated Aug. 20, 2014.

* cited by examiner

MULTI-SITE VIDEO BASED COMPUTER AIDED DIAGNOSTIC AND ANALYTICAL PLATFORM

RELATED APPLICATIONS

This application claims priority from U.S. Provisional Patent Application No. 61/800,316 filed on Mar. 15, 2013, which is herein incorporated by reference.

FIELD OF THE INVENTION

The present invention relates to a data sharing platform, and more particularly, this invention relates to a multi-site video based data sharing platform and method of using said platform.

BACKGROUND

In the medical field, different medical examinations require varying levels of expertise. For example, a vaccine may be administered by a registered nurse, while a routine check-up may be performed by any Doctor of Medicine (MD) for humans or Doctor of Veterinary Medicine for animal, and complicated surgeries are typically only performed by a practitioner with additional years of specialized training. It follows that some members of the medical field are revered as "specialists" whose expertise may extend into multiple arenas within the medical field.

In many instances, specialists are not present during more routine examinations, e.g., such as an ultrasound. However, depending on the instance, a specialist's expertise may be desired. In some cases, the facts of the particular instance may be beyond the scope of knowledge for the person administering the examination, while in other cases, a second opinion may be desired. Regardless of the particular reason for seeking additional assistance, the person (e.g., specialist) giving the additional assistance may not be able to be physically present where the examination is being performed. It follows that without additional information about or contact with the patient, absent specialists are not able to develop informed opinions in such situations.

SUMMARY

A method according to one embodiment includes receiving a stream of biometric imaging data of a patient; receiving medical data about the patient; receiving a video stream depicting a source of the biometric imaging data; receiving supplemental information selected from a group consisting of: a second video stream depicting a human, one or more use cases corresponding to the biometric imaging data, an image of anatomy comparable to the biometric imaging data; and preparing for simultaneous output to a graphical user interface on a single display screen: the biometric imaging data, the medical data about the patient, the video stream depicting a source of the biometric imaging data, and the supplemental information. Each of the biometric imaging data, the medical data about the patient, the video stream depicting a source of the biometric imaging data, and the supplemental information is simultaneously output in a unique region of the graphical user interface.

A method according to another embodiment includes receiving biometric imaging data from a medical device; transmitting a stream of the biometric imaging data of a patient to a remote location: transmitting a video stream depicting a source of the biometric imaging data; receiving instructions to alter an acquisition characteristic of the biometric imaging data from the remote location; and outputting the instructions to alter the acquisition characteristic of the biometric imaging data.

A method according to yet another embodiment includes receiving from a first location via a network a stream of biometric imaging data of a patient, wherein the biometric imaging data includes ultrasound sonograph data; receiving medical data about the patient; receiving a video stream depicting a source of the biometric imaging data; receiving supplemental information selected from a group consisting of: a second video stream depicting a human, one or more use cases corresponding to the biometric imaging data, an image of anatomy comparable to the biometric imaging data; preparing for simultaneous output on a graphical user interface on a single display screen at a second location that is remote from the first location: the biometric imaging data, the medical data about the patient, the video stream depicting a source of the biometric imaging data, and the supplemental information; and sending the biometric imaging data, the medical data about the patient, the video stream depicting a source of the biometric imaging data, and the supplemental information to a device having the display screen at the second location. Each of the biometric imaging data, the medical data about the patient, the video stream depicting a source of the biometric imaging data, and the supplemental information is simultaneously output in a unique region of the graphical user interface. The method further includes receiving user input from the first location for controlling a device acquiring the ultrasound sonograph data; and sending the user input to the second location of the source of the biometric imaging data.

Other aspects and advantages of the present invention will become apparent from the following detailed description, which, when taken in conjunction with the drawings, illustrate by way of example the principles of the invention.

BRIEF DESCRIPTION OF THE DRAWINGS

For a fuller understanding of the nature and advantages of the present invention, as well as the preferred mode of use, reference should be made to the following detailed description read in conjunction with the accompanying drawings.

DETAILED DESCRIPTION

Figure 1A:
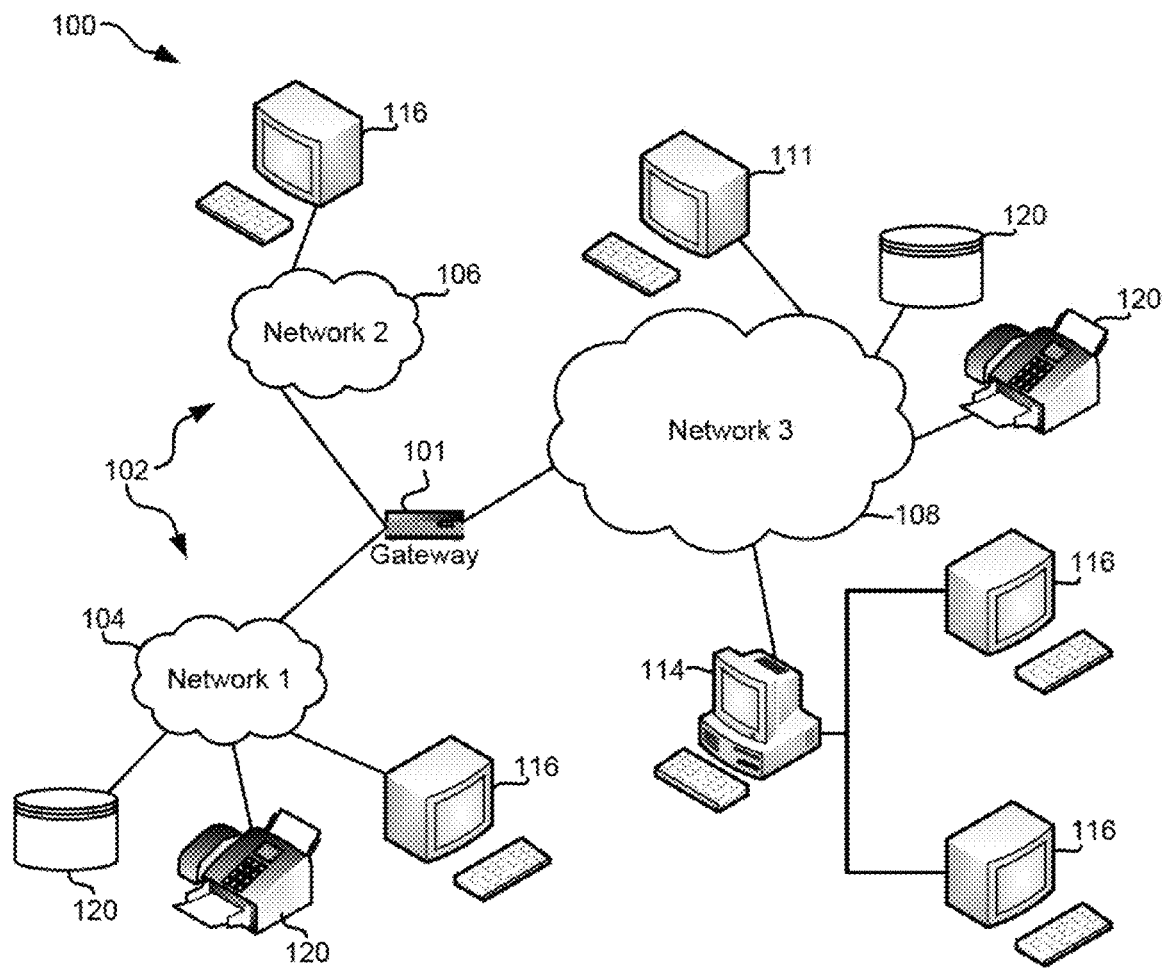
FIG. 1A is a diagram of a network architecture according to one embodiment.

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

The following description discloses several preferred embodiments of a multi-site video based data sharing platform and/or related systems and methods of using said platform. Various data sharing platforms presented herein include a connection for transferring medical data between a patient and a specialist. Moreover, data received by the specialist is preferably presented on a multi-function split screen that may implement any of the features described in further detail below. As used herein, a "patient" may refer to a human or an animal.

In one general embodiment, a method includes receiving a stream of biometric imaging data of a patient; receiving medical data about the patient; receiving a video stream depicting a source of the biometric imaging data; receiving supplemental information selected from a group consisting of: a second video stream depicting a human, one or more use cases corresponding to the biometric imaging data, an image of anatomy comparable to the biometric imaging data; and preparing for simultaneous output to a graphical user interface on a single display screen: the biometric imaging data, the medical data about the patient, the video stream depicting a source of the biometric imaging data, and the supplemental information. Each of the biometric imaging data, the medical data about the patient, the video stream depicting a source of the biometric imaging data, and the supplemental information is simultaneously output in a unique region of the graphical user interface.

In another general embodiment, a method includes receiving biometric imaging data from a medical device; transmitting a stream of the biometric imaging data of a patient to a remote location; transmitting a video stream depicting a source of the biometric imaging data; receiving instructions to alter an acquisition characteristic of the biometric imaging data from the remote location; and outputting the instructions to alter the acquisition characteristic of the biometric imaging data.

In yet another general embodiment, a method includes receiving from a first location via a network a stream of biometric imaging data of a patient, wherein the biometric imaging data includes ultrasound sonograph data; receiving medical data about the patient; receiving a video stream depicting a source of the biometric imaging data; receiving supplemental information selected from a group consisting of: a second video stream depicting a human, one or more use cases corresponding to the biometric imaging data, an image of anatomy comparable to the biometric imaging data; preparing for simultaneous output on a graphical user interface on a single display screen at a second location that is remote from the first location: the biometric imaging data, the medical data about the patient, the video stream depicting a source of the biometric imaging data, and the supplemental information, and sending the biometric imaging data, the medical data about the patient, the video stream depicting a source of the biometric imaging data, and the supplemental information to a device having the display screen at the second location. Each of the biometric imaging data, the medical data about the patient, the video stream depicting a source of the biometric imaging data, and the supplemental information is simultaneously output in a unique region of the graphical user interface. The method further includes receiving user input from the first location for controlling a device acquiring the ultrasound sonograph data; and sending the user input to the second location of the source of the biometric imaging data.

The description herein is presented to enable any person skilled in the art to make and use the invention and is provided in the context of particular applications of the invention and their requirements. Various modifications to the disclosed embodiments will be readily apparent to those skilled in the art and the general principles defined herein may be applied to other embodiments and applications without departing from the spirit and scope of the present invention. Thus, the present invention is not intended to be limited to the embodiments shown, but is to be accorded the widest scope consistent with the principles and features disclosed herein.

In particular, various embodiments of the invention discussed herein are implemented using the Internet as a means of communicating among a plurality of computer systems. One skilled in the art will recognize that the present invention is not limited to the use of the Internet as a communication medium and that alternative methods of the invention may accommodate the use of a private intranet, a Local Area Network (LAN), a Wide Area Network (WAN) or other means of communication. In addition, various combinations of wired, wireless (e.g., radio frequency) and optical communication links may be utilized.

The program environment in which one embodiment of the invention may be executed illustratively incorporates one or more general-purpose computers or special-purpose devices such hand-held computers. Details of such devices (e.g., processor, memory, data storage, input and output devices) are well known and are omitted for the sake of clarity.

It should also be understood that the techniques of the present invention might be implemented using a variety of technologies. For example, the methods described herein may be implemented in software running on a computer system, or implemented in hardware utilizing one or more processors and logic (hardware and/or software) for performing operations of the method, application specific integrated circuits, programmable logic devices such as Field Programmable Gate Arrays (FPGAs), and/or various combinations thereof. In one illustrative approach, methods described herein may be implemented by a series of computer-executable instructions residing on a storage medium such as a physical (e.g., non-transitory) computer-readable medium. In addition, although specific embodiments of the invention may employ object-oriented software programming concepts, the invention is not so limited and is easily adapted to employ other forms of directing the operation of a computer.

The invention can also be provided in the form of a computer program product comprising a computer readable storage or signal medium having computer code thereon, which may be executed by a computing device (e.g., a processor) and/or system. A computer readable storage medium can include any medium capable of storing computer code thereon for use by a computing device or system, including optical media such as read only and writeable CD and DVD, magnetic memory or medium (e.g. hard disk drive, tape), semiconductor memory (e.g., FLASH memory and other portable memory cards, etc.), firmware encoded in a chip, etc.

A computer readable signal medium is one that does not fit within the aforementioned storage medium class. For example, illustrative computer readable signal media communicate or otherwise transfer transitory signals within a system, between systems e.g., via a physical or virtual network, etc.

FIG. 1A illustrates an architecture 100, in accordance with one embodiment. As an option, the present architecture 100 may be implemented in conjunction with features from any other embodiment listed herein, such as those described with reference to the other FIGS. Of course, however, such architecture 100 and others presented herein may be used in various applications and/or in permutations which may or may not be specifically described in the illustrative embodiments listed herein. Further, the architecture 100 presented herein may be used in any desired environment.

As shown in FIG. 1A, a plurality of remote networks 102 are provided including a first remote network 104 and a second remote network 106. A gateway 101 may be coupled between the remote networks 102 and a proximate network 108. In the context of the present network architecture 100, the networks 104, 106 may each take any form including, but not limited to a LAN, a WAN such as the Internet, public switched telephone network (PSTN), internal telephone network, etc.

In use, the gateway 101 serves as an entrance point from the remote networks 102 to the proximate network 108. As such, the gateway 101 may function as a router, which is capable of directing a given packet of data that arrives at the gateway 101, and a switch, which furnishes the actual path in and out of the gateway 101 for a given packet.

Further included is at least one data server 114 coupled to the proximate network 108, and which is accessible from the remote networks 102 via the gateway 101. It should be noted that the data server(s) 114 may include any type of computing device/groupware. Coupled to each data server 114 is a plurality of user devices 116.

Such user devices 116 may include a desktop computer, laptop computer, hand-held computer, printer or any other type of logic. It should be noted that a user device 111 may also be directly coupled to any of the networks, in one embodiment.

A peripheral 120 or series of peripherals 120, e.g. facsimile machines, printers, networked storage units, etc., may be coupled to one or more of the networks 104, 106, 108. It should be noted that databases, servers, and/or additional components may be utilized with, or integrated into, any type of network element coupled to the networks 104, 106, 108. In the context of the present description, a network element may refer to any component of a network.

According to some approaches, methods and systems described herein may be implemented with and/or on virtual systems and/or systems which emulate one or more other systems, such as a UNIX system which emulates a MAC OS environment, a UNIX system which virtually hosts a MICROSOFT WINDOWS environment, a MICROSOFT WINDOWS system which emulates a MAC OS environment, etc. This virtualization and/or emulation may be enhanced through the use of VMWARE software, in some embodiments.

In more approaches, one or more networks 104, 106, 108, may represent a cluster of systems commonly referred to as a "cloud." In cloud computing, shared resources, such as processing power, peripherals, software, data processing and/or storage, servers, etc., are provided to any system in the cloud, preferably in an on-demand relationship, thereby allowing access and distribution of services across many computing systems. Cloud computing typically involves an Internet or other high speed connection (e.g., 4G LTE, fiber optic, etc.) between the systems operating in the cloud, but other techniques of connecting the systems may also be used.

Figure 1B:
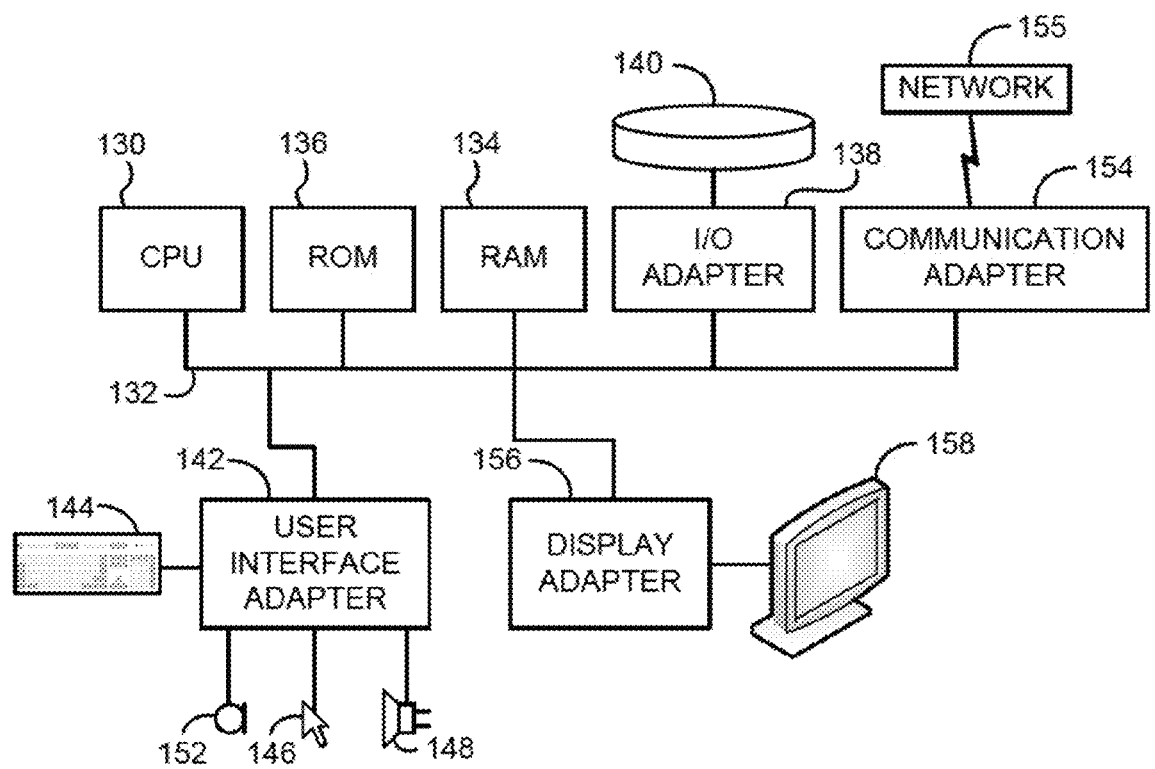
FIG. 1B is a representative hardware environment according to one embodiment.

FIG. 1B shows a representative hardware environment associated with a user device 116 and/or server 114 of FIG. 1A, in accordance with one embodiment. Such figure illustrates a typical hardware configuration of a workstation having a central processing unit 130, such as a microprocessor, and a number of other units interconnected via a system bus 132.

The workstation shown in FIG. 1B includes a Random Access Memory (RAM) 134, Read Only Memory (ROM) 136, an I/O adapter 138 for connecting peripheral devices such as disk storage units 140 to the bus 132, a user interface adapter 142 for connecting a keyboard 144, a mouse 146, a speaker 148, a microphone 152, and/or other user interface devices such as a touch screen and a digital camera (not shown) to the bus 132, communication adapter 154 for connecting the workstation to a communication network 155 (e.g., a data processing network) and a display adapter 156 for connecting the bus 132 to a display device 158.

The workstation may have resident thereon an operating system such as the Microsoft WINDOWS Operating System (OS), a MAC OS, a UNIX OS, etc. It will be appreciated that a preferred embodiment may also be implemented on platforms and operating systems other than those mentioned. A preferred embodiment may be written using JAVA, XML, C, and/or C++ language, or other programming languages, along with an object oriented programming methodology. Object oriented programming (OOP), which has become increasingly used to develop complex applications, may be used.

As previously mentioned, in the medical field, different medical examinations require varying levels of expertise. For example, a vaccine may be administered by a registered nurse, while a routine check-up may be performed by any Doctor of Medicine (MD), and complicated surgeries may only be performed by a practitioner with additional years of specialized training. It follows that some members of the medical field are revered as "specialists" whose expertise may extend into multiple arenas within the medical field.

In many instances, specialists are not present during more routine examinations, e.g., such as an ultrasound. However, depending on the instance, a specialist's expertise may be desired. Regardless of the particular reason for seeking additional assistance, the person (e.g., specialist) giving the additional assistance may not physically be present where the examination is being performed. It follows that without additional information about or contact with the patient, absent specialists are not able to develop informed opinions in such situations.

In sharp contrast, various embodiments herein present a multi-site video-based data sharing platform that allows for transfer of data corresponding to a number of different applications. For example, medical records for a patient in addition to a live video feed of an examination being performed on the patient may be made available to a specialist at a remote location, as will be described in further detail below. Moreover, it should be noted that although many of the embodiments and/or examples described herein pertain to the medical field, any of such embodiments and/or examples may be applied to other subject areas such as information technology (IT), military applications, etc. as would be apparent to one skilled in the art armed with the teachings presented herein.

Figure 2:
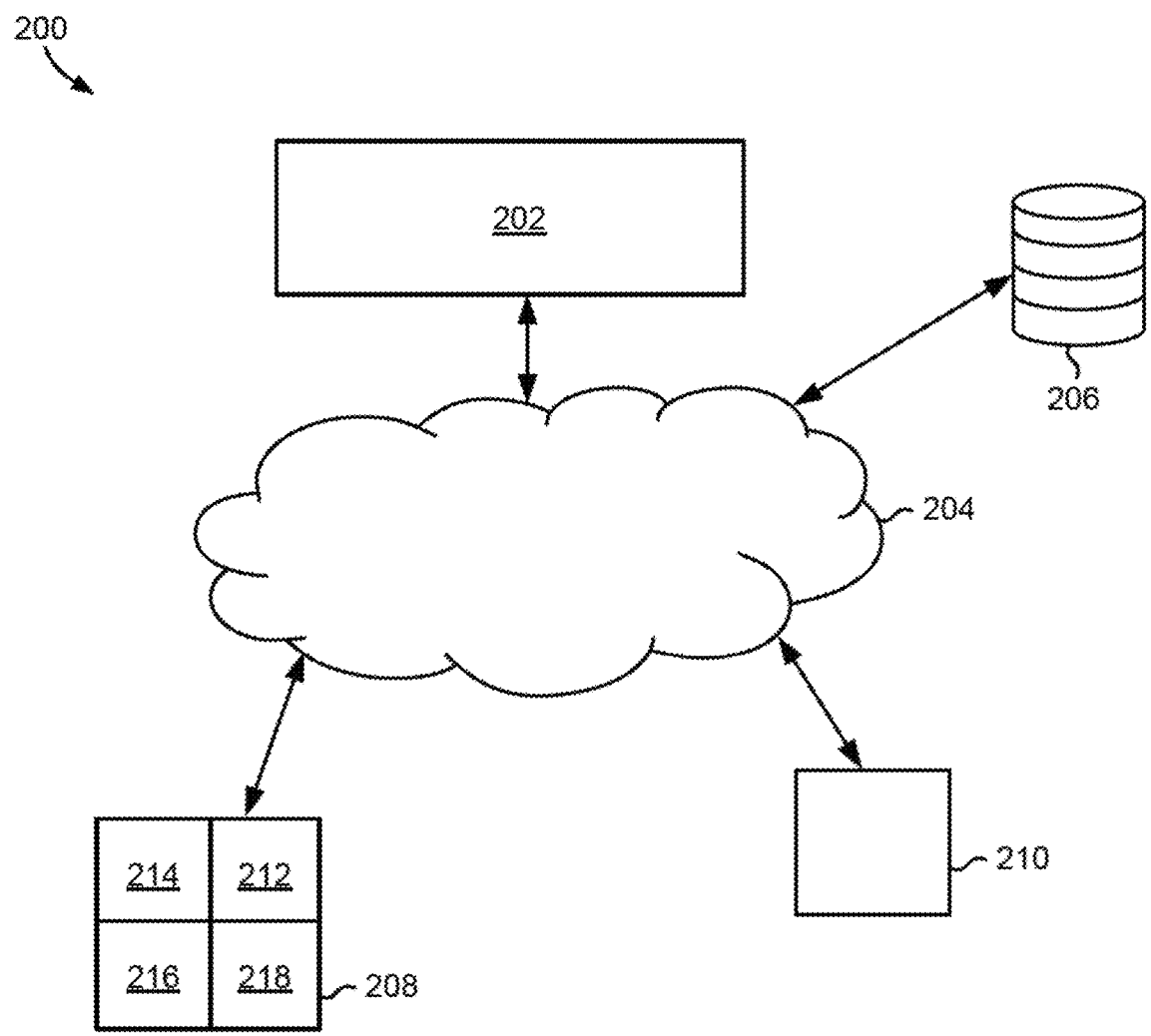
FIG. 2 is a representational diagram of a network implementing a data sharing platform according to one embodiment.

FIG. 2 depicts an exemplary network 200 that implements a multi-site data sharing platform, in accordance with one embodiment. As an option, the present network 200 may be implemented in conjunction with features from any other embodiment listed herein, such as those described with reference to the other FIGS. Of course, however, such network 200 and others presented herein may be used in various applications and/or in permutations which may or may not be specifically described in the illustrative embodiments listed herein. Further, the network 200 presented herein may be used in any desired environment. Thus FIG. 2 (and the other FIGS.) should be deemed to include any and all possible permutations.

Looking to FIG. 2, the network 200 includes a remote server 202 connected to a cloud based computing environment 204. A storage database 206 is also connected to the cloud based computing environment 204. Storage database 206 may include any type of storage memory, including, but not limited to, tape based storage, disk based storage, etc.

Referring still to FIG. 2, graphical user interface 208 and device 210 are additionally connected to the cloud based computing environment 204.

As will be described in further detail below, the graphical user interface 208 is preferably positioned at the location of a user (e.g. a specialist), while the device 210 is preferably positioned at the location of a patient. Device 210 may include any device that may be connected to the cloud based computing environment 204, either physically (e.g., an Ethernet cable) or wirelessly, that may be used to perform a medical procedure. For example, which is in no way intended to limit the invention, the device 210 may be a computing device that is in communication with a sonogram probe used to perform sonogram examinations on patients.

It follows that the network 200 desirably allows for data to be transferred between a specialist at a remote location and persons at a patient's location, e.g. via the cloud based computing environment 204. For example, if someone were conducting an ultrasound exam on a patient, by transferring data between the graphical user interface 208 at a specialist's location and the device 210 at the patient's location, network 200 has the ability to relay guidance given from a specialist at a remote location, to an individual (e.g., technician) conducting an ultrasound examination on the patient. Such guidance may include adjusting focus of the image being relayed, highlighting conspicuous sections on the patient, etc., as will be described in further detail below.

Moreover, being coupled to a storage database 206 allows for various information to be accessed throughout the network 200, e.g., such as a patient's medical history and/or information relating to various medical conditions. Furthermore, the cloud based computing environment 204 allows for such data to be available to both a specialist at a remote location, and persons at the patient's location.

The graphical user interface 208 may include any desired graphical user interface, as the network 200 is preferably compatible with various devices. For example, graphical user interface 208 may include personal computers (PCs), laptops, tablets, servers, etc. However, in preferred embodiments, the graphical user interface 208 has four display windows 212, 214, 216, 218 corresponding to unique regions of the graphical user interface 208. In such embodiments, each of the display windows 212, 214, 216, 218 may present a unique set of data pertaining to a particular task. Illustrative examples of display windows presenting unique sets of data on unique regions thereof are described in further detail below, e.g., see FIGS. 3A-4B.

Referring still to FIG. 2, it follows that the network 200 preferably provides real time data with secure delivery thereof. According to various embodiments, data may be transferred using H.264/DICOM/TWAIN, multimedia electronic medical records (EMR) deploying advanced protocol converters, virtually lossless packet delivery and rapid integration with LAN/WAN and/or SANs, etc.

Network 200 may further include store and forward functionality. Moreover, various approaches may include wireless and/or wireline interfaces to communicate with vital sign monitoring devices, video conferencing equipment, cloud based systems (e.g., see 204), etc. Further still, some embodiments described herein may include the ability to provide advanced network management features using self-healing and/or self-learning functionalities, as will be described in further detail below.

Figure 3A:
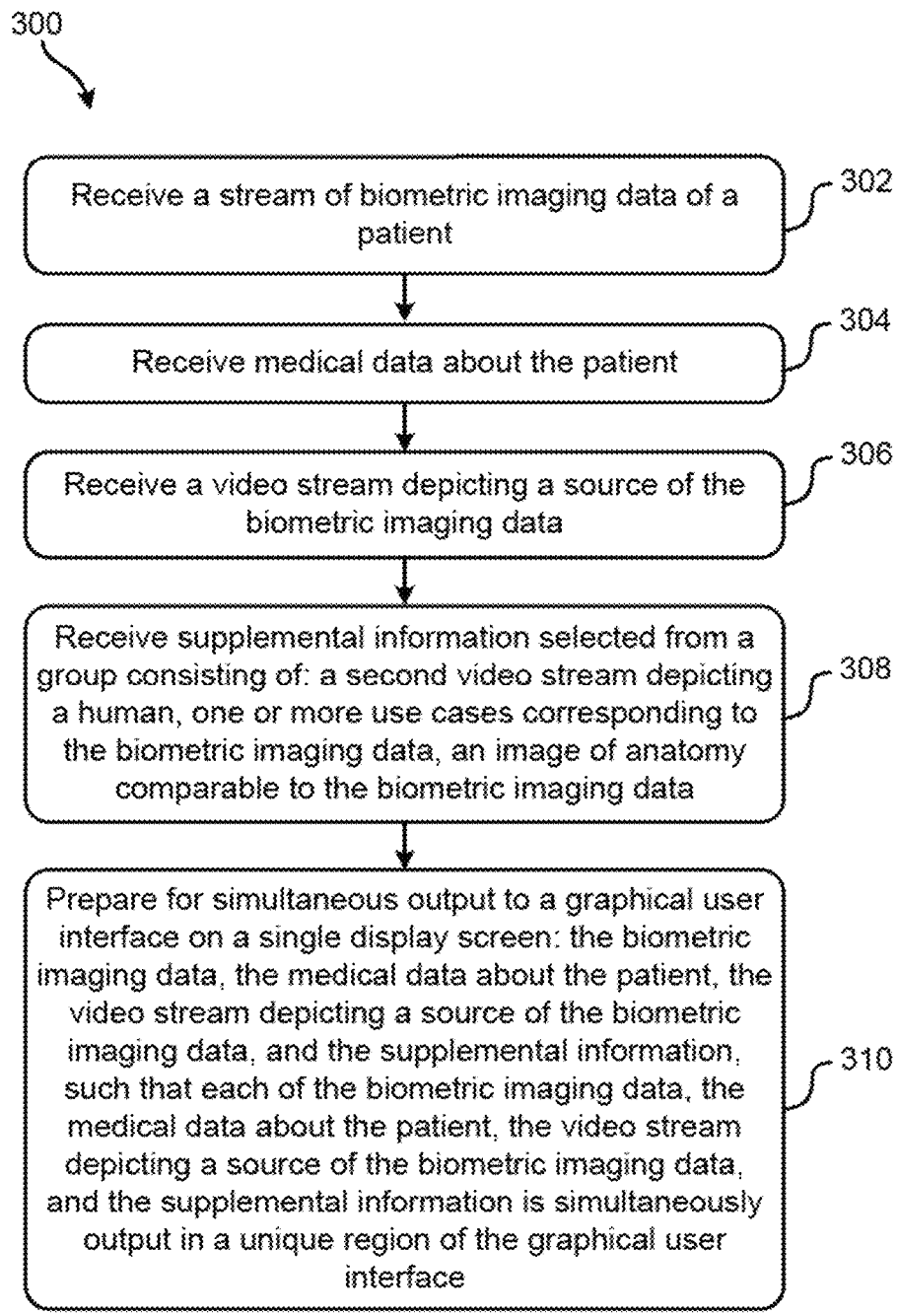
FIG. 3A is a flowchart of a method according to one embodiment.

FIG. 3A depicts a method 300, in accordance with one embodiment. It should be noted that the operations of method 300 are intended to be performed using recipient side platform software operations and/or EEM server(s). In other words, looking momentarily to FIG. 2, the operations of method 300 are intended to be performed at the graphical user interface 208 location, e.g., pertaining to a specialist's remote location. However, this is in no way intended to limit the invention. In other embodiments, any of the operations of method 300 may be tailored to be implemented and/or performed at a patient side of a network, e.g., such as network 200 of FIG. 2.

Referring again to FIG. 3A, as an option, the present method 300 may be implemented in conjunction with features from any other embodiment listed herein, such as those described with reference to the other FIGS., such as FIG. 2. Of course, however, such method 300 and others presented herein may be used in various applications and/or in permutations which may or may not be specifically described in the illustrative embodiments listed herein. Further, the method 300 presented herein may be used in any desired environment. Thus FIG. 3A (and the other FIGS.) should be deemed to include any and all possible permutations.

Looking now to FIG. 3A, method 300 includes receiving a stream of biometric imaging data of a patient. See operation 302. Moreover, operation 304 includes receiving medical data about the patient, e.g., from a storage database. In some approaches, the medical data about the patient may be stored in a storage database performing the recipient side platform software operations of method 300. However, in other approaches, the medical data about the patient may be stored in a remote storage database that may be a remote server (e.g., see 202 of FIG. 2).

Referring still to FIG. 3A, depending on the application, the patient may be a human or an animal. Furthermore, in different approaches, the biometric imaging data may include data pertaining to any type of medical examination. For example, in some embodiments the biometric imaging data may include ultrasound sonograph data, while in other embodiments, the biometric imaging data may include radiography data. It follows that one or more of the operational steps of method 300 may be implemented for various different medical examinations.

Furthermore, operation 306 includes receiving a video stream depicting a source of the biometric imaging data, while operation 308 includes receiving supplemental information selected from a group consisting of: a second video stream depicting a human (e.g., secondary specialist, etc.), one or more use cases corresponding to the biometric imaging data, an image of anatomy comparable to the biometric imaging data.

Referring still to method 300 of FIG. 3A, operation 310 includes preparing for simultaneous output to a graphical user interface on a single display screen: the biometric imaging data, the medical data about the patient, the video stream depicting a source of the biometric imaging data, and the supplemental information. Moreover, each of the biometric imaging data, the medical data about the patient, the video stream depicting a source of the biometric imaging data, and the supplemental information are preferably simultaneously output in a unique region of the graphical user interface. Thus, as described above, a graphical user interface may have unique regions (windows), each of which present a unique set of data pertaining to a particular task.

Although in the embodiment corresponding to FIG. 3A the unique regions of the graphical user interface are assigned one of the biometric imaging data, the medical data about the patient, the video stream depicting a source of the biometric imaging data, and the supplemental information, in other embodiments, each of the unique regions may display a different set of data. In some instances, a person accessing the graphical user interface (e.g., a specialist) may be able to choose which set(s) of data are displayed at each of the unique regions. Thus, the data displayed on the graphical user interface may depend on the specialist's preferences, a patient's condition, etc.

Furthermore, it is preferred that the stream of biometric imaging data is received in real time concurrently with the video stream. Thus, the specialist receiving the information may be able to make real time analysis of data gathered from multiple sources.

In addition to receiving data, it may be greatly beneficial to provide the specialist with the ability to provide input corresponding to a particular situation. For example a specialist may wish to change one or more settings of the device acquiring the biometric imaging data, such as the depth, frequency, etc. of an ultrasound probe. Moreover, a specialist may wish to change one or more settings of the video stream, provide instructions to a technician shown in the video stream, control an angle of a video camera providing the video stream, etc.

Accordingly, the specialist may provide feedback via the graphical user interface using a mouse, touchscreen inputs, keyboard inputs, etc. Moreover, graphical elements such as dials, sliders, numerical fields, etc. may be shown on the screen and manipulated by the user. Such inputs are transmitted to the patient-side system where the feedback is applied.

As a result, the specialist may be able to exert more control over and gather more valuable information pertaining to the examination being conducted, and thereby provide a more informed diagnosis/recommendation. It follows that method 300 of FIG. 3A may additionally include an operation of sending user input to a location of the source of the biometric imaging data, e.g., to enable any of the approaches described immediately above. Although not required, this additional operation may allow for greater functionality of method 300.

In other embodiments, changes may be made to the supplemental information by the specialist and/or a technician performing an examination on the patient. According to the present description, "changes" may include adding additional data, making alterations to existing data, deleting existing data, etc., depending on the desired embodiment. According to one example, upon viewing an examination of a patient via the graphical user interface described above, a specialist may add a supplemental report to the results of the examination.

It follows that any changes made to the supplemental information may further be sent to a remote server (e.g., see 202 of FIG. 2) for saving said changes. Upon being sent to a remote server, the changes made to the supplemental information may be saved to a storage database (e.g., see 206 of FIG. 2) and/or sent to the patient's location. Moreover, depending on the changes made, the data corresponding to the changes made to the supplemental information may be saved over existing data, appended to existing data, used to amend existing data, etc., or any other data management operation which would be apparent to one skilled in the art upon reading the present description.

For embodiments in which the supplemental information includes a second video stream depicting a human (e.g., secondary specialist, medical practitioner, family member of the patient, etc.), the human depicted in the second video stream also preferably has access to the information of at least one of the information displays of the graphical user interface. Thus, depending on the desired embodiment, the human (e.g., secondary specialist, medical practitioner, family member of the patient, etc.) depicted in the second video stream may have access to one or more of the biometric imaging data, the medical data about the patient, the video stream depicting a source of the biometric imaging data, and the supplemental information.

Figure 3B:
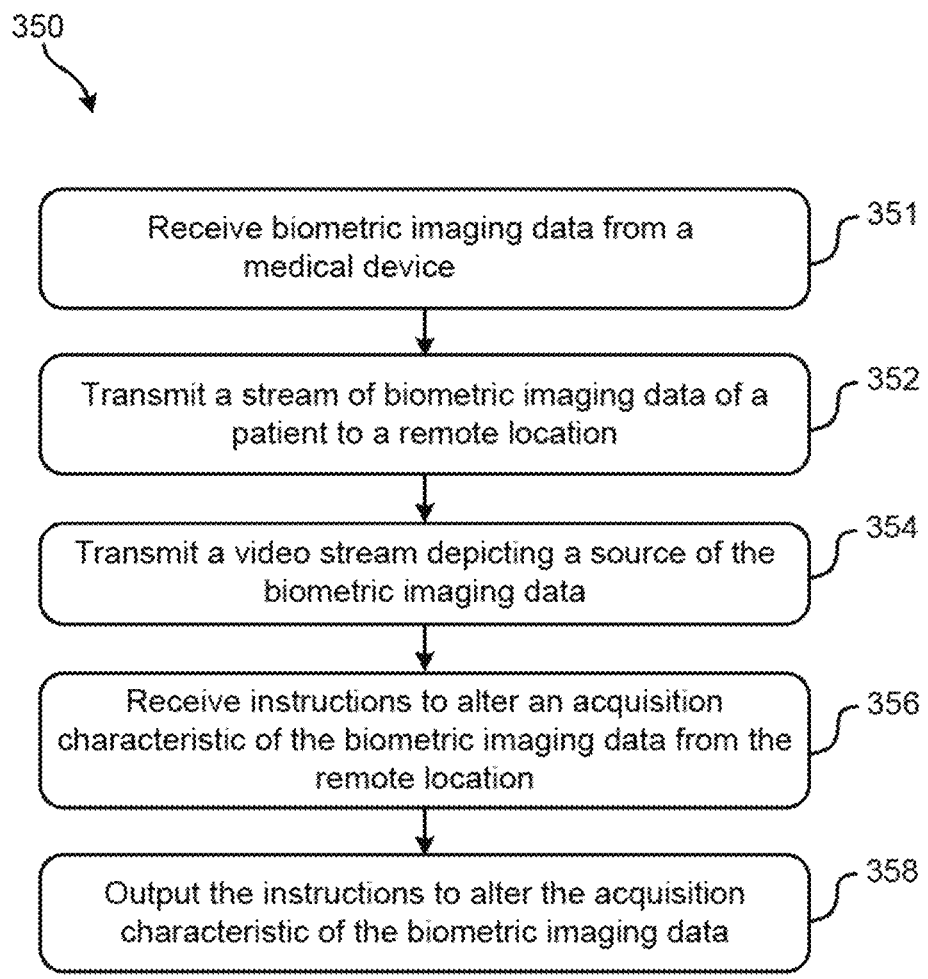
FIG. 3B is a flowchart of a method according to one embodiment.

FIG. 3B depicts a method 350, in accordance with one embodiment. For the present embodiment, it should be noted that the operations of method 350 are intended to be performed on patient side platform software operations and/or EEM server(s). In other words, looking momentarily to FIG. 2, the operations of method 350 are intended to be performed at the device 210 location, e.g., pertaining to a patient's location. However, this is in no way intended to limit the invention. In other embodiments, any of the operations of method 350 may be tailored to be implemented and/or performed at a patient side of a network, e.g., such as network 200 of FIG. 2.

Referring again to FIG. 3B, as an option, the present method 350 may be implemented in conjunction with features from any other embodiment listed herein, such as those described with reference to the other FIGS., such as FIG. 2. Of course, however, such method 350 and others presented herein may be used in various applications and/or in permutations which may or may not be specifically described in the illustrative embodiments listed herein. Further, the method 350 presented herein may be used in any desired environment. Thus FIG. 3B (and the other FIGS.) should be deemed to include any and all possible permutations.

Referring now to FIG. 3B, biometric imaging data is received from a medical device such as an ultrasound device in operation 351. Operation 352 of method 350 includes transmitting a stream of biometric imaging data of a patient (human or animal) to a remote location such as the specialist location and/or a remote server (e.g., see 206 of FIG. 2). The biometric imaging data is preferably compressed and transmitted at a rate of less than 800 kilobytes per second, and in some embodiments less than 800 kilobits per second. This allows for a large amount of information to be transmitted from a patient site while minimizing the power, bandwidth requirements, etc. to perform such data transmissions.

In different approaches, the biometric imaging data may include data pertaining to any type of medical examination. For example, in some embodiments the biometric imaging data may include ultrasound sonograph data, while in other embodiments, the biometric imaging data may include radiography data. It follows that one or more of the operational steps of method 350 may be implemented for various different medical examinations.

Moreover, it is preferred that the stream of biometric imaging data is transmitted in real time concurrently with the video stream. Thus, a specialist that may be receiving the information may be able to make real time analysis of data gathered from multiple sources (e.g., see method 300 above).

Referring still to FIG. 3B, method 350 includes transmitting a video stream depicting a source of the biometric imaging data. See operation 354. This may allow an individual at a remote location to view a technician as they conduct a medical examination on a patient. According to an example, the video stream may be taken from a video camera positioned in the corner of a room in which a medical examination is administered to a patient. Thus, a remote specialist may be able to view the medical examination as it is taking place as if they were standing in the same room.

Furthermore, operation 356 of FIG. 3B includes receiving instructions to alter an acquisition characteristic of the biometric imaging data from the remote location. Moreover, operation 358 includes outputting the instructions to alter the acquisition characteristic of the biometric imaging data. As mentioned above, a remote specialist may be viewing a medical examination conducted on a patient. However, during the examination, the specialist may wish to guide a technician conducting the examination. Thus, it is desirable that the specialist is able to present instructions which are receivable at the patient's location to be performed automatically by an operating system and/or by a person (e.g., the technician) at the patient's location.

Depending on the embodiment, the instructions may include any number of a range of different directions. In one approach, the instructions may include control instructions from a user (e.g., specialist) at the remote location. Thus, the instructions may be output to a device acquiring the biometric imaging data. However, in another approach, the instructions may include live voice instructions from a user (e.g., specialist) at the remote location. In such an approach, the live voice instructions are preferably audibly output, but are not limited thereto. The live voice instructions may be presented to the patient site on a graphical user interface via text, images, pictures, video, real time display of a specialist's pen strokes on a smart surface, etc.

Figure 3C:
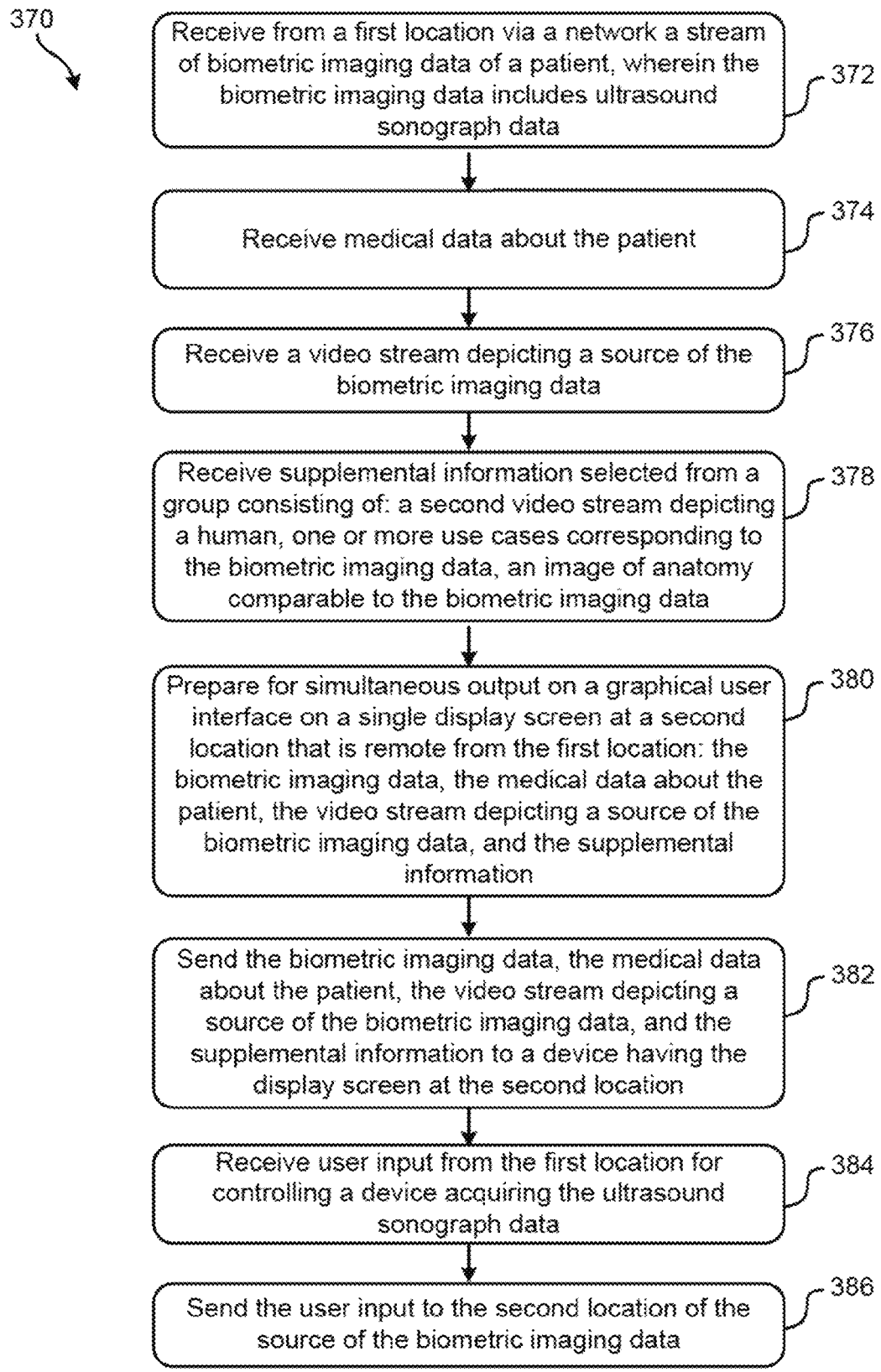
FIG. 3C is a flowchart of a method according to one embodiment.

FIG. 3C depicts a method 370 that may be implemented by a cloud-based system that may coordinate the sharing of data according to one embodiment.

As an option, the present method 370 may be implemented in communication with features from any other embodiment listed herein, such as those described with reference to the other FIGS., such as FIG. 2. Of course, however, such method 370 and others presented herein may be used in various applications and/or in permutations which may or may not be specifically described in the illustrative embodiments listed herein. Further, the method 370 presented herein may be used in any desired environment. Thus FIG. 3C (and the other FIGS.) should be deemed to include any and all possible permutations.

In operation 372, a stream of biometric imaging data of a patient is received from a first location, e.g., patient site, via a network. In this example, the biometric imaging data includes ultrasound sonograph data. In operation 374, medical data about the patient is received, and a video stream depicting a source of the biometric imaging data is received in operation 376. Supplemental information selected from a group consisting of: a second video stream depicting a human, one or more use cases corresponding to the biometric imaging data, an image of anatomy comparable to the biometric imaging data is received in operation 378. In operation 380, the following are prepared for simultaneous output on a graphical user interface on a single display screen at a second location that is remote from the first location: the biometric imaging data, the medical data about the patient, the video stream depicting a source of the biometric imaging data, and the supplemental information. The biometric imaging data, the medical data about the patient, the video stream depicting a source of the biometric imaging data, and the supplemental information is sent to a device having the display screen at the second location in operation 382. Each of the biometric imaging data, the medical data about the patient, the video stream depicting a source of the biometric imaging data, and the supplemental information is simultaneously output in a unique region of the graphical user interface. In operation 384, user input is received from the first location for controlling a device acquiring the ultrasound sonograph data. In operation 386, the user input is sent to the second location of the source of the biometric imaging data.

In one approach, the image of anatomy comparable to the biometric imaging data may be automatically selected based on an analysis of the biometric imaging data, without receiving user input. Such image may be of healthy anatomy, diseased anatomy, injured anatomy, etc. The selected image is then sent to the second location. Image recognition algorithms of a type known in the art may be used to automatically select the biometric imaging data. Moreover, a user may specify a region of interest in the sonogram data, and the system may use the specified region to perform the search.

Figure 4A:
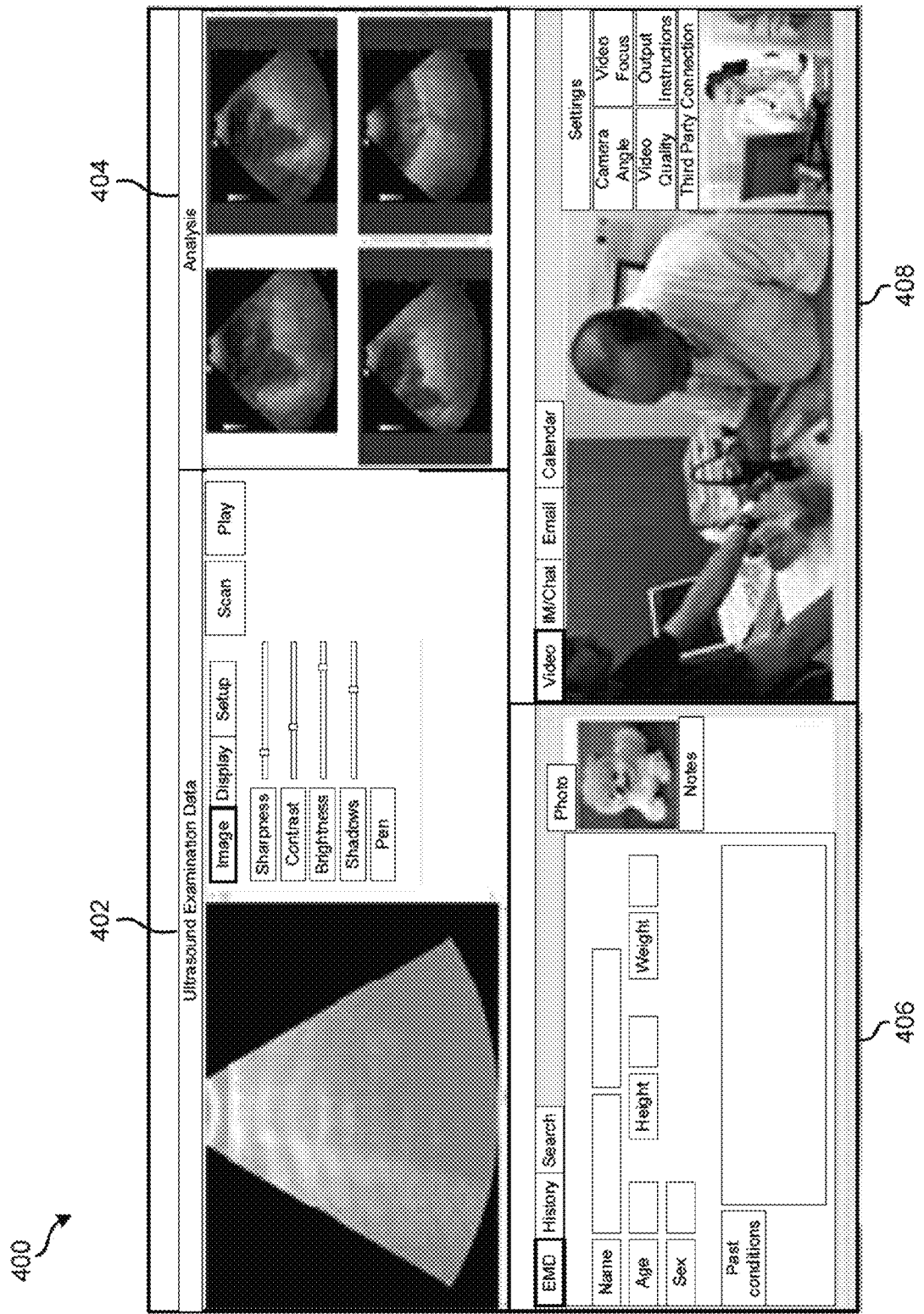
FIG. 4A is a graphical user interface according to one embodiment.
Figure 4B:
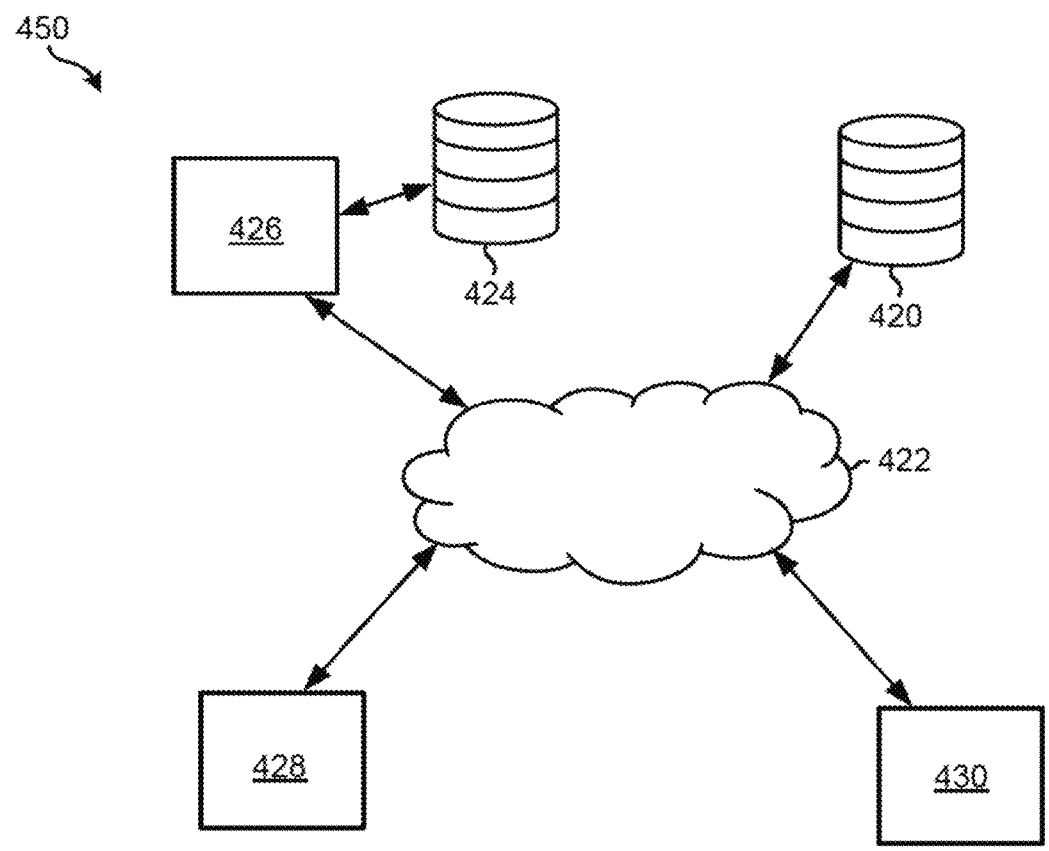
FIG. 4B is a conceptual diagram of a data sharing platform according to one embodiment.

Looking to FIG. 4A, an in-use example of a graphical user interface 400 is depicted according to an illustrative embodiment. Moreover, FIG. 4B illustrates a conceptual diagram of a data sharing platform 450 carrying out a 3-way on-demand examination that may correspond to the in-use example of FIG. 4A. As an option, the embodiments illustrated in FIGS. 4A-4B may be implemented in conjunction with features from any other embodiment listed herein, such as those described with reference to the other FIGS. Thus FIGS. 4A-4B (and the other FIGS.) should be deemed to include any and all possible permutations.

Referring now to FIGS. 4A-4B, the content displayed in the different windows of the graphical user interface 400 (e.g., screen) corresponds to an ultrasound examination on an animal which is taking place at a clinic 426.

Upon being brought to the clinic, the animal (e.g., pet) may be registered by a receptionist. If the animal is an existing patient, the receptionist may retrieve the medical information (e.g., electronic health record) corresponding to the animal, which may be stored in a cloud based storage environment 422. However, if the animal is a new patient, medical information corresponding to the animal may be collected, registered and stored in a local server 424 and/or at a remote storage database 420.

When a Doctor of Veterinary Medicine (DVM) examines the animal at the clinic, the DVM may decide that the animal requires an ultrasound, e.g., due to an ailing condition. Following conventional workflow, the clinic would be required to make an appointment with a radiologist a few days in the future from the date of the current visit.

However, in sharp contrast, the various embodiments described herein allow for a much more efficient workflow. Following techniques described herein the DVM may chose a Diplomat of the American College of Veterinary Radiology (DAVCR) from a list of DAVCRs in the clinic's database, e.g., which may be stored on-site and/or in a remote data storage system. At the same time, a technician may prepare the animal for the desired ultrasound examination.

After the DVM selects one of the on-call DAVCR, the data sharing platform 450 may automatically set up a video conferencing and collaboration session with pet's EHR sent to both the clinic 426 and the DAVCR at a remote location 428 (e.g., if already available). Thus, the DAVCR may authenticate that pet requires an ultrasound examination, and may further guide the DVM in carrying out the ultrasound exam. As mentioned below, the data sharing platform may provide additional examination guidance to the DVM, such as an ideal level of pressure applied on the body of the animal by the probe, a preferred angle of contact, automatic adjustment to a preferred depth into the animal based on the preliminary conditions and/or the DAVCR's recommendation, etc.

As described above, a camera may provide a live feed of the DVM's actions during the examination to the DAVCR. The camera may be integrated with a laptop and/or desktop and may further be optionally adjustable to meet the DAVCR's desired settings. However, in some embodiments, a camera may not be used as the DAVCR may only need to view the reproduced ultrasound image.

Looking to the graphical user interface 400 in FIG. 4A, the DAVCR (specialist) has different data presented on each of the windows 402, 404, 406, 408 at a remote site. Looking first to window 402, ultrasound imaging is relayed from the clinic where the ultrasound is being performed, through a data sharing platform, to the DAVCR. The DAVCR may mark the ultrasound imaging, e.g., using an interface tool to denote an area of interest. Upon marking the ultrasound imaging, the screen shot may be frozen, whereby the ultrasound imaging and the DAVCR's markings may automatically be uploaded to a remote storage database 420 (e.g., see 206 of FIG. 2), a cloud based computing environment 422 (e.g., see 204 of FIG. 2), a local storage database 424, the DVM directly via a graphical user interface at the clinic 426, etc. Furthermore, cine loop may also be also stored. Controls are provided to enable the user to adjust ultrasound system characteristics such as sharpness, contrast, etc. in real time.

Looking now to window 404, imaging of normal (e.g., healthy) anatomy comparable to the area(s) of interest in the animal may be displayed. Depending on the embodiment, the imaging of the normal anatomy may be used by the DAVCR to compare to the area of interest in the animal, e.g., to assist in determining whether further examination is necessary.

Furthermore, window 406 displays EMRs of the animal that may be accessed from a remote storage database (e.g., see 206 of FIG. 2), a cloud based computing environment (e.g., see 204 of FIG. 2), an on-site storage database, etc. Thus, the DAVCR is able to easily examine any medical information pertaining to the animal that may be of interest/pertinent their analysis of the present ultrasonic examination.

Window 408 displays supplemental information which, according to the present embodiment, includes a video output from a camera at the clinic that is capturing the DVM as they perform the ultrasound examination, preferably in real time. As a result, the DAVCR is able to coach the DVM as they perform the examination by providing instructions to alter the acquisition characteristics of the examination.

Window 408 also illustrates an additional video input which displays a second specialist. The second specialist may be desired in situations where the DAVCR requires a second opinion, the EMR is incomplete, the area of interest involves a situation unfamiliar to the DAVCR, etc. Regardless of the reason, the additional video input prompts a three way video conferencing session to be established. The second specialist's site 430 may be immediately authenticated and all the relevant information may thereby be provided to the second specialist.

Once the second specialist has provided an input satisfactory to the DAVCR and/or DVM, the second specialist's input may be time stamped and added to a storage database 420 as seen in FIG. 4B. Records may be kept in the storage database 420 for about five years, but may be longer or shorter depending on the desired embodiment.

Referring again to FIG. 4A, once the DAVCR has provided their input (e.g., prognosis, prescriptions, etc.), they may signs off (e.g., disconnect from the data sharing network). In some approaches, different sessions may be recorded and stored in a storage database, e.g., a cloud based storage network. Moreover, EMD files may be updated automatically to reflect the DAVCR's input (e.g., prognosis, prescriptions, etc.) and/or any resolved issues. Thus, if the DVM desires to access an updated record of the animal's up-to-date EMD, they may be accessed and/or downloaded from the storage database, e.g., a cloud based storage network.

In view of the description of the present embodiment, four windows of a graphical user interface according to different embodiments may include one or more of a video of the DVM performing the examination on the patient, frozen or cine screen of the marked area (expanded), a view of a normal (e.g., healthy) subject or cine loop, and DAVCR or specialist alternating on DVM screen with audio explanation.

In some approaches, the windows 402, 404, 406, 408 may be moved, resized, maximized, minimized, etc.

In various applications, a data sharing network/platform, e.g., as illustrated in FIG. 2, may be flexible enough to handle several sessions simultaneously. The network is constantly monitoring itself for any problems in the background of any running tasks such as video conferencing task for multiple sites; displaying up to four video windows on a single PC, laptop or tablet for real time sessions; web conferencing, multicast commutations from one sender to many receivers; information exchange of text-based messages, voice and video chat to be shared simultaneously, across geographically dispersed locations; web conferencing include meetings, training events, lectures, or short presentations from any computer; etc.

These network capable tasks are beneficial as they provide sophisticated plug and play capabilities to users. For example, during a medical examination of a patient, rather than requiring a user to study the intricacies of the data, the self-learning ability of certain embodiments allows for system based software (computer aided diagnostics) to recognize and flag high interest data regions. For instance, an inconspicuous spot on an organ may be detected and flagged by a computer aided diagnostic program, indicating that further examination is required, e.g., by a specialist.

It follows that such computer aided diagnostic programs may be incorporated with storage databases with data pertaining to various types of medical cases and educational information. These storage databases may be implemented in cloud based storage systems (e.g., see 204 of FIG. 2) and/or back-end storage databases (e.g., see 206 of FIG. 2). Storage databases having medical cases and educational information may be accumulated over several years, thereby aiding a user (e.g., non-specialist or technician) in detecting problematic locations quickly rather than having the remote specialist guiding the user during each examination.

Computer aided diagnostic programs may additionally provide a user with patient specific examination information such as probe pressure needed to be applied, automatic operational frequency and/or depth adjustments, resolution of the image, the cine loop, etc. In some instances, a window corresponding to the computer aided diagnostic program may indicate that a probe being used in the examination has been positioned at the location corresponding to a flagged location. The program may further freeze the display on the screen to automatically zoom in on the flagged location for increased detail. Moreover, the storage databases and/or EMRs for the patient may also be simultaneously updated.

According to another approach, a high fidelity explanation of the probable causes for a flagged location may be provided when a comparison is made between the flagged area and a corresponding normal (e.g., healthy) anatomy comparable to the flagged area. Moreover, the high fidelity explanation may be presented to a user (e.g., technician and/or specialist) audibly via a speaker and/or visually, e.g., via a ticker tape at the bottom of a screen to provide text.

Figure 4C:
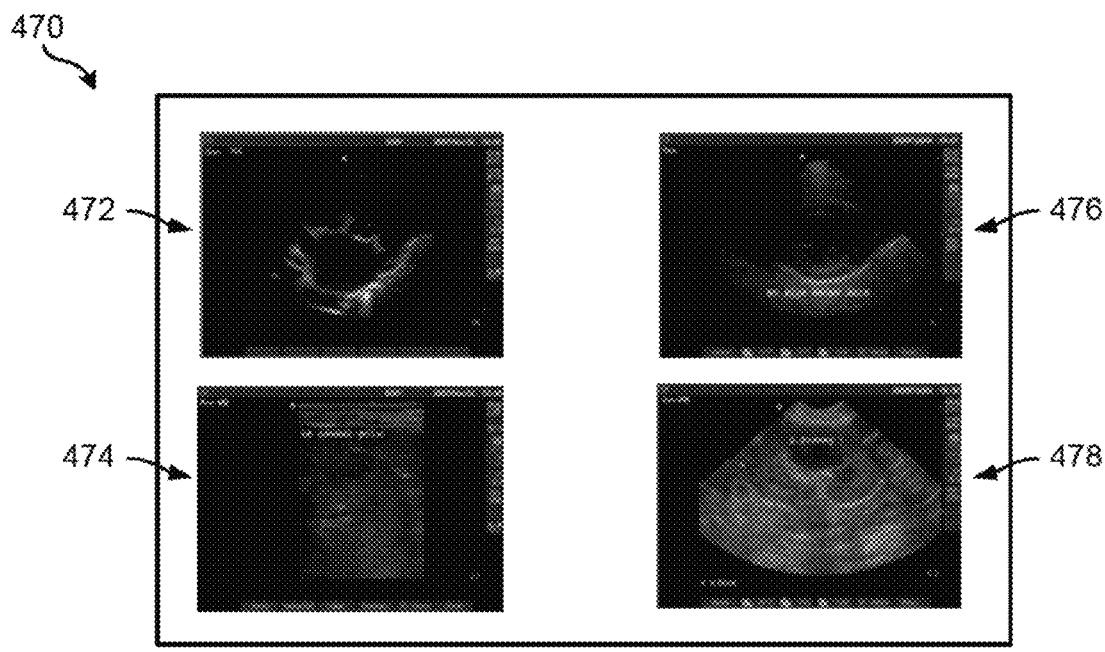
FIG. 4C is a display platform according to one embodiment.

Looking momentarily to FIG. 4C, an exemplary platform 470 is illustrated to show the comparison between a patient's flagged area, and a corresponding normal (e.g., healthy) anatomy comparable to the flagged area. Although two flagged areas 472, 474 and two corresponding normal anatomy views 476, 478 are illustrated in the present embodiment, other implementations may include different numbers of paired flagged areas and normal anatomy views, e.g., depending on the number of flagged areas for the given patient.

Computer aided diagnostic programs may also deliver critical medical information to physicians, technicians, sonographers, nurses, etc. Various embodiments herein may include one or more libraries that may access a subset of the web. It follows that computer aided diagnostic programs have the intelligence to retrieve a best-fit solution to a problem as opposed to countless search result hits as produced by internet search engines. Moreover, by retrieve a best-fit solution to a problem, computer aided diagnostic programs may also function as a virtual teacher of sorts, in view of its inherent ability to cater for desired education and/or prognosis.

An illustrative example of a software architecture used to manage the network 200, and/or to implement one or more of the method steps of either of the methods 300, 350, may have three layers as follows. A first layer may include an application layer which supports processing of Extensible Markup Language (XML) and/or Extensible HyperText Markup Language (XHTML) application messages. Moreover, a second layer may include a system and network layer which supports the system resource management, network management and routing functions. In addition, the second layer may support network switching, security and QoS functions. An illustrative list of such functions, which is in no way intended to limit the invention, may include, but is not limited to any of the following:

a. Full wire speed layer 2 and layer 3 switching at one or more port b. Standard layer 2 support: spanning tree, 802.1Q VLANs, 802.1 P multicast groups and prioritized services.

c. Standard layer 3 support: ICMP, OSPF, PIM, and IP multicast, MPLS.

d. Network QoS functions: 802.1P, IP TOS, DiffServ e. Support redundant network configurations f. Systems and Applications monitoring and statistics gathering g. Security support with IPSec tunneling and transport functions h. LDAP Service interface.

Finally, the third layer of the software architecture may include an interface layer that provides protocol interfaces support for WiFi, Ethernet, 3G/4G, DSL, Satellite, etc.

Multi-site data sharing platforms as disclosed herein provide a number of desirable features. For example, the physical level transport as described herein facilitates redundancy using well-established back up algorithms that resemble "Self-healing" ring transmission architectures. Additionally, intelligent transaction recovery with built-in transaction caching allows for transactions to be rolled back and resubmitted to backup servers.

Built-in XML transaction processors are also able to speed up secure and/or non-secure XML-based application transactions, while built-in secure "Virtual Pipe" embodiments are also achievable, where data are encrypted using an advanced encryption standard (AES).

Telemedicine Bandwidth Management is defined as capabilities to meter, log, and control bandwidth usage among different hospitals, clinics, applications, and content types. "Virtual Pipes" are used in different embodiments to share bandwidth of WAN pipe in the multi-services network. "Virtual Pipes" are defined using the physical port. VLAN, source or destination IP address, TCP or UDP port number, URL, HTTP cookie, etc. Moreover, an administrator may define the data rates for each of the "Virtual Pipes" using one or more of a committed information rate (the minimum supported rate), a soft limit (the maximum data rate allowed), and a hard limit (the maximum data rate allowed before data are dropped). In some approaches, if a soft limit is exceeded, the data may still be transported, however, the user may be warned and/or receive an added charge.

The data rate can be simulated at each "Virtual Pipe" and each "Virtual Pipe" is preferably regulated individually according to the data rate. To facilitate content routing, packets may be classified based on one or more of IP addresses, TCP/UDP port numbers, IP precedence (e.g., 3 bits in the type of service field of the IP packet header), URL and sub-URL, and/or MAC addresses. Once the data packets are classified and marked with a unique identification (e.g., using the TOS field in the IP (IPv4) header and/or a priority field of a IPv6 header), based on the classification, the data packet may be treated accordingly when forwarding to the destination. In other words, a data packet may be processed differently depending on the classification it is marked with.

Figure 5:
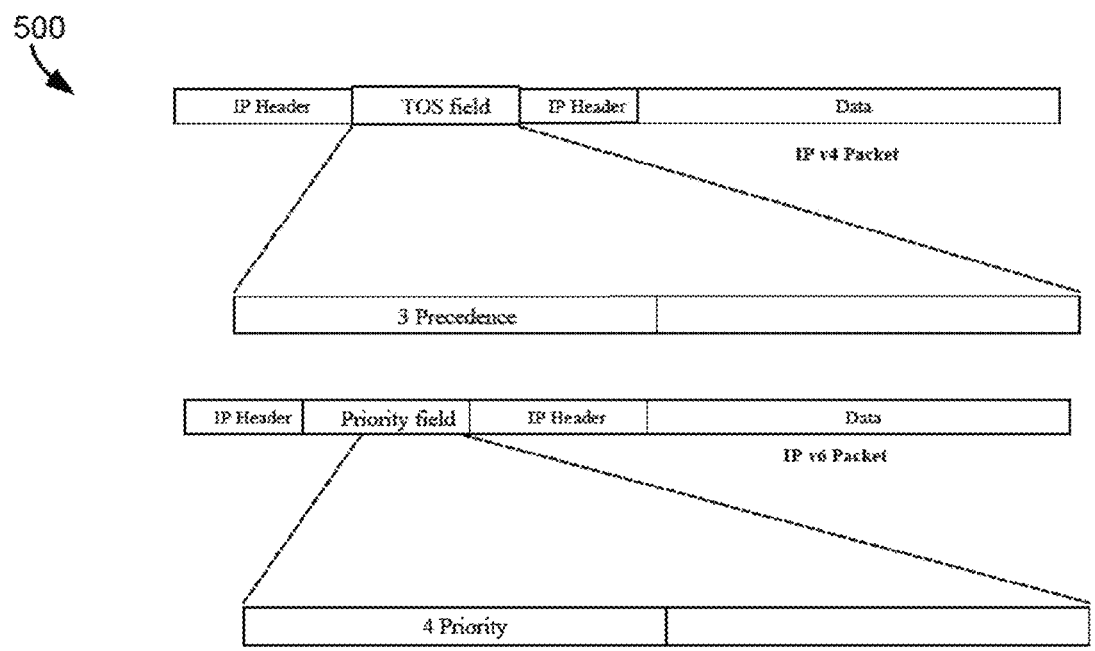
FIG. 5 is a priority field of IP packets according to two different embodiments.

FIG. 5 depicts an exemplary priority field 500, in accordance with one embodiment. As an option, the present priority field 500 may be implemented in conjunction with features from any other embodiment listed herein, such as those described with reference to the other FIGS. Of course, however, such priority field 500 and others presented herein may be used in various applications and/or in permutations which may or may not be specifically described in the illustrative embodiments listed herein. Further, the priority field 500 presented herein may be used in any desired environment. Thus FIG. 5 (and the other FIGS.) should be deemed to include any and all possible permutations.

Looking to FIG. 5, a priority field 500 of two different IP packets is illustrated in accordance with one embodiment. As illustrated, a unique identification of 3 precedence may be assigned to a data packet using the TOS field of an IPv4 packet header. Similarly, a unique identification of 4 priority is assigned to a data packet using a priority field of a IPv6 packet header.

It follows that packets may be classified as data flows into different queues. Moving forward, the bandwidth allocation to a given data packet during traffic congestion is based on the class or priority of each queue.

Various embodiments described herein are also capable of performing policy-based networking and routing to resolve congestion in the network, in addition to active networking functions, e.g., to support national and/or local application workload balancing. Application redirection to cache servers may also be achieved, in addition to multicast support for multimedia streaming and/or load balancing of servers.

In order to support load-balancing for telemedicine servers, data sharing platforms, as disclosed herein (e.g., see 200 of FIG. 2), preferably monitor the health and performance of the computer systems, e.g., in a server farm that supports the platform. Different embodiments will incorporate knowledge of each server and may perform server selection decisions based on the server's health; performance; available resources, e.g., such as disk, memory, CPU load, etc.; etc. According to some approaches, a server's health check may include server's disk I/O, memory capacity and/or CPU utilization. Moreover, in preferred applications, failed or overloaded servers will be bypassed when processing user request redirection.

Furthermore, web-based remote management facilities are achievable that allow management of local and national SEP networks at central location and/or through a cloud network. Extensive access control facilities may also be imposed to restrict illegal access to the management functions.

A server's performance statistics are vital to provide quick response to a user and address any SLA (Service Level Agreement) issues that may be relevant to an exemplary in-use embodiment. The performance statistics may include, but are not limited to, application response time, number of hits, individual server response times, connection statistics, etc. Moreover, the server performance statistics may be gathered by a remote monitoring agent (RMON) loaded on the servers, e.g., of conventional construction. In one approach, a RMON agent may serve as a background process that collects server statistics and reports the statistics to a data sharing platform periodically.

In addition to server performance statistics gathering, a data sharing platform may perform health check functions on the server connectivity, server health, and application health (e.g., of a web server). It is preferred that application level health checks are performed for the following illustrative list of applications: FTP, HTTP, SMTP, NNTP. For situations dealing with customer applications, an agent may be installed on the server to perform health checks on the applications, e.g., using a SNMP interface.

To perform load balancing among servers, it is preferred that a data sharing platform perform network address translation between the virtual servers and the real servers selected.

Figure 6:
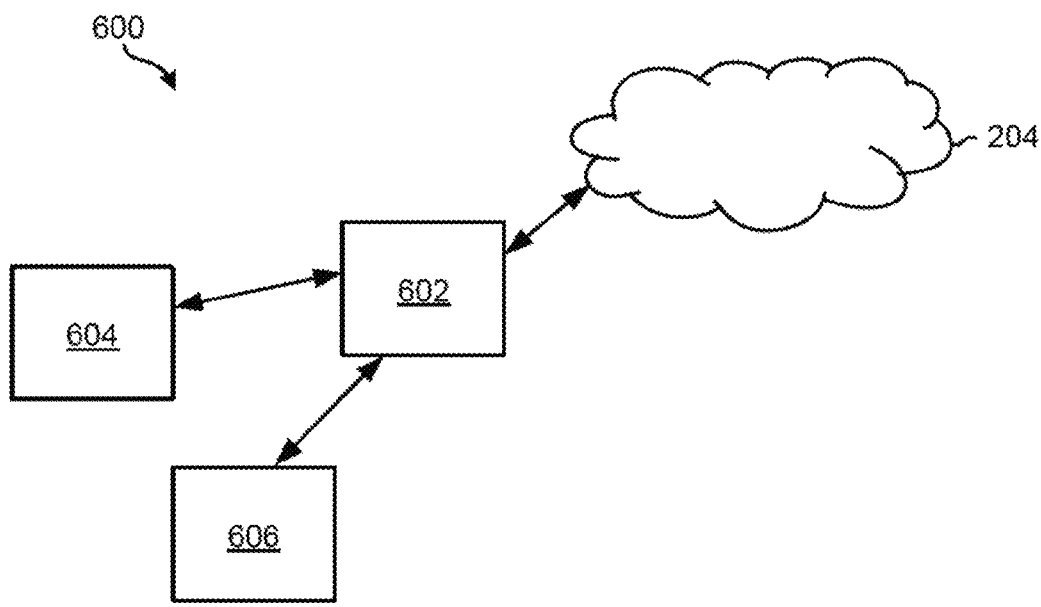
FIG. 6 is a data sharing platform having a data packet processing engine according to one embodiment.

FIG. 6 depicts an exemplary data sharing platform 600 having a data packet processing engine 602. As an option, the data sharing platform 600 may be implemented in conjunction with features from any other embodiment listed herein, such as those described with reference to the other FIGS. Of course, however, such data sharing platform 600 and others presented herein may be used in various applications and/or in permutations which may or may not be specifically described in the illustrative embodiments listed herein. Further, the data sharing platform 600 presented herein may be used in any desired environment. Thus FIG. 6 (and the other FIGS.) should be deemed to include any and all possible permutations.

As illustrated, data packet processing engine 602 is connected to a cloud based computing environment 204 which may include any of the approaches described herein. Data packet processing engine 602 is also connected to users at two distinct locations 604, 606.

Depending on the desired embodiment, the data packet processing engine 602 may include layered engines, multimedia gateways, VPN management, application multicasting, etc., or any other desired functionality which would be apparent to one skilled in the art upon reading the present description.

Moreover, data packet processing engine 602 may implement different qualities of service to each of the users at locations 604 and 606, e.g., corresponding to an exemplary service plan. For example, the user at location 604 may pay for a higher quality of service than the user at location 606. According to various approaches, quality of service may include data download rates, data upload rates, functionality, etc., or any other service that may be scaled, e.g., based on a payment level.

Quality of service is also important in many embodiments to determine whether a network is able to distinguish the data traffic and assign the appropriate resources for mission-critical and/or time-sensitive applications. Depending on the desired use, a user may prioritize service classes based on IP data content, web content and/or application data content. In addition to the content type, the quality of service may also be applied to the link level bandwidth control (e.g., at each interface port).

Figure 7:
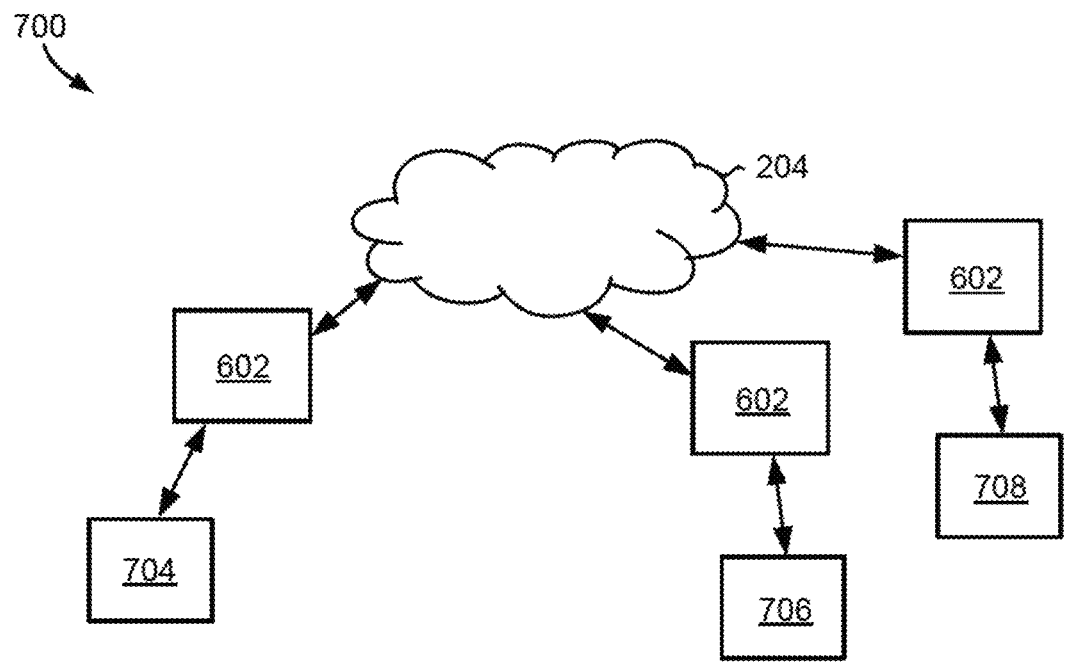
FIG. 7 is a picture archiving and communications system according to one embodiment.

Looking now to FIG. 7, a Picture Archiving and Communications System (PACS) 700 is illustrated according to an exemplary embodiment. As an option, the PACS 700 may be implemented in conjunction with features from any other embodiment listed herein, such as those described with reference to the other FIGS. Of course, however, such PACS 700 and others presented herein may be used in various applications and/or in permutations which may or may not be specifically described in the illustrative embodiments listed herein. Further, the PACS 700 presented herein may be used in any desired environment. Thus FIG. 7 (and the other FIGS.) should be deemed to include any and all possible permutations.

It should be noted that the various components of PACS 700 are in no way intended to limit the invention, but rather are presented by way of example only.

As illustrated, the PACS 700 includes a cloud based computing environment that is connected to packet processing engines 602. Moreover, each of the packet processing engines 602 are connected to a respective client 704, 706, 708.

The PACS 700 may include multicast capability, e.g., depending on the desired embodiment. It follows that in some approaches, multicast services may be provided for instances of disaster recovery, enterprise clustering (e.g., server, storage, real-time e-business, inventory management, etc.), etc.

Furthermore, PACS 700 may have additional functionality, including the ability to detect application specific traffic within VPN and convert such traffic into smart packets. According to another approach, PACS 700 may be able to perform multicasts to other data sharing platforms and possibly retransmit when there are instances of errors. In yet another approach, PACS 700 may support multicasting for any content type, e.g., file based, block based, stream based, broadcast, etc.

Referring still to FIG. 7, depending on the desired embodiment, packet processing engines 602 may analyze packet sizes, convert packets into smaller sized packets (e.g., compress packets), prioritize packet processing, facilitate unicast and/or multicast delivery of packets, resend out-of-sequence packets, process smart packets (e.g., tags of a type known in the art), prioritize smart packets, deliver smart packets, calculate round-trip delay for delivering packets, etc.

Content in PACS 700 may be classified as either static content or dynamic content. Examples of static content include, but are not limited to, text, picture, audio, logos, templates, video clips, etc., while dynamic content may include any content generated by executing scripts and/or applets. It follows that static content may be processed using low-end servers and dynamic content may be processed using high-performance servers. According to the present description, "low-end servers" are intended to mean servers having performance characteristics at least lower than those of the high-performance servers.

However, servers can become overloaded when large numbers of concurrent connections and/or requests are directed to the same server. It follows that load balancing functions may be implemented in various embodiments presented herein. According to preferred approaches, load balancing functions offer an easy way to distribute the processing load to multiple servers without impacting a client using the servers or the network architecture itself. In addition, load balancing functions may further provide a redundant server network that is resistant to failure.

In such embodiments, a data sharing platform may act as a front-end for the servers and may additionally be assigned with a Virtual IP address (VIP) which may serve as the address that is used by the external world. Thus, when a client sends requests to the server, the VIP address is used. The data sharing platform is responsible for determining the "best available" server to send the requests to, e.g., by performing load balancing on TCP packets. Illustrative operations performed by the data sharing platform may include switching a received SYN request, finding a best server, binding the server IP to session, and/or updating VIP with IP and MAC address with server's MAC address.

Different embodiments described herein include performing load balancing operations. According to one approach, load balancing on UDP packets may include a data sharing platform providing a session control for UDP traffic (e.g. because UDP does not support session control). Moreover, the session may be opened within a user specified period of time. However, according to various other approaches, load balancing may incorporate one or more of the following:
a. Least utilized or "most available" server selection
b. "Most available" server is defined as either one of the following:
c. Simple least connections
d. Weighted least connections
e. Simple round-robin
f. Weighted round-robin For a traditional data center setup, firewall systems sit in the data path between the external Internet and internal data networks. However, such firewalls significantly reduce the speed of Internet communication in view of the fact that every data packet has to be inspected before being forwarded to the Internet network domain. Traditional firewalls can also become the single point of failure in these traditional data center network setups.

In sharp contrast, firewall load balancing functions may be established in any of the embodiments described herein to distribute data traffic to multiple firewalls. As a result, multiple firewall systems are able to share the load in filtering out data packets waiting to be allowed to enter the data center network. Additionally, the embodiments described herein may perform firewall health check functions. During such firewall health check functions, if a firewall system fails, the data sharing platform preferably directs the data traffic to the remaining firewall systems. As a result, these firewall load balancing functions desirably eliminate the single-point-of-failure issues seen in traditional data center network setups.

Some embodiments may incorporate web caching which desirably improves user response time when accessing the Internet. For intranet, caching can speed up the retrieval time when accessing content across wide-area private network. The idea is to move the content as close to the web clients as possible.

However, a drawback experienced in traditional caching configurations is that a client usually has only one active path between the cache server and the Internet. Since the cache server in such traditional configurations is required to filter out the cloud traffic from the non-cloud traffic and forward the request to the Internet, the cache server becomes the bottleneck in the network.

Conversely, web cache redirection as used in the various embodiments herein includes a method which moves web cache servers from the data path between the client and Internet. In addition, web cache redirection may also provide load-balancing capability for the web cache servers. The switch examines all packets, redirecting cloud packets to pre-specified caches, while non-cloud traffic is switched to its destination at the data link layer.

In order to support load balancing for servers, data sharing platform preferably monitor the health and performance of the computer systems in the servers therein. As previously mentioned, the data sharing platform may incorporate knowledge of each server and make server selection decisions based on the server's health, performance, and available resources (such as disk, memory, and CPU load). According to an illustrative approach, the server's health check may include server's disk I/O, memory capacity, and/or CPU utilization. Moreover, the data sharing platform preferably bypasses failed or overloaded servers when processing user request redirection.

Data sharing platforms may further implement server aware functions. For such functions, the data sharing platform may load balance application requests to different application processes on different servers. Thus, the data sharing platform may be responsible for setting up application sessions and provides session control and/or management functions for five different types of sessions.

A first type of session includes a TCP session. A TCP session is set up between a client and a particular application or web server. All traffic associated with a TCP session is preferably forwarded to the same server.

A second type of session includes a UDP session. UDP is connectionless protocol; therefore, there is no guarantee of successful transfer of an UDP datagram. When an UDP application, such as NFS, transmits large UDP datagrams, the datagrams are fragmented into smaller packets before being sent to the destination. In order to provide proper switching on UPD data, sessions are preferably assigned to UDP data and UDP fragments of the same sessions will be forwarded to the same server.

A third type of session includes persistent session. Applications, such as Internet searches, may require multiple TCP connections to the same server. As a result, the SEP is required to acquire the knowledge of these applications and support persistent sessions while switching.

Furthermore, a fourth type of session includes a SSL session. Any secured transaction using SSL protocol is preferably treated as a SSL session. By using the "SSL Session ID", a data sharing platform may distinguish SSL transactions from other clients. However, in some approaches, the data sharing platform may be required to decode the SSL information to distinguish the source of the secure transaction.

Finally, a fifth type of session corresponding to the data sharing platform may include a "co-browsing" session. According to some examples, e-business applications may require multiple connections between two hosts. It follows that a persistent session, such as "co-browsing", may be required to keep track of the state of the visiting client site, and a SSL session to support secured transactions for purchasing. In such embodiments, it is desirably that a data sharing platform understand the "co-browsing" session in order provide proper switching control.

Denial of Service (DoS) attacks to servers exposed to the Internet is a serious problem facing the Internet business community. Deficiencies in the TCP/IP protocol suite of conventional systems have allowed attackers to launch multiple denial-of-service attacks on commercial sites. As a result, these denial-of-service attacks have significantly reduced processing speed of such conventional sites, thereby resulting in significant losses.

In sharp contrast, various embodiments herein are desirably capable of identifying the source of the data and encapsulating the data from the same source to a virtual pipe. Such capabilities are desirably able to prevent the aforementioned denial-of-service attacks. By identifying the source of the data and encapsulating the data from the same source to a virtual pipe, the impact from the denial-of-service attacks on the network will be restricted to a small number of virtual pipes and servers. Thus, the overall network and servers will not be negatively affected. In addition, policies may be established to warn administrators about possible attacks based on traffic patterns.

Figure 8:
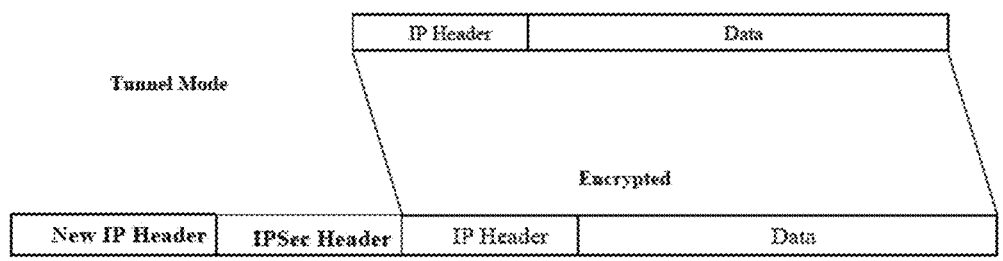
FIG. 8 is a representational diagram of sets of headers within a network according to one embodiment.
Figure 8:
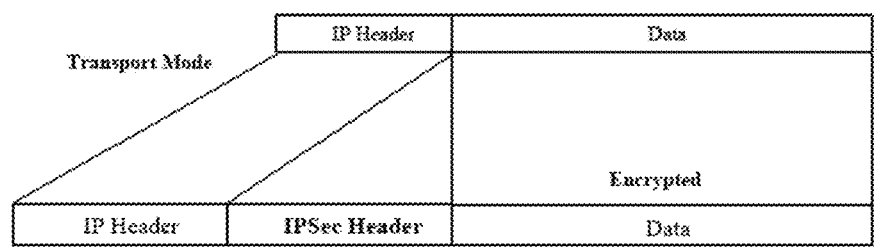

Data integrity and security within the network is preferably provided using the IPSec as defined in IETF standards. IPSec identifies a new set of headers to be inserted into the IP datagrams as illustrated in FIG. 8. These headers desirably provide information for securing the payload of the IP packet.

In different embodiments, the IPSec may operate in a tunnel mode and/or a transport mode. In tunnel mode, the IP datagram may be encrypted and is encapsulated within a new frame with a new IP header and an IPSec header. Moreover, the router will forward the new packet to the destined router where the destined router will forward the IP datagram based on the original IP header.

Alternatively, in transport mode, only the data portion of the IP datagram is encrypted and the IPSec header is inserted between the IP Header and the data. It follows that in transport mode, the encrypted data will be decrypted when passed to the destination host.

For IPSec support, data sharing platforms described herein will preferably incorporate industry-standard authentication algorithms, e.g., such as MD5 or the Secure Hash Algorithm (SHA); and/or encryption algorithms, e.g., such as DES. In further approaches, data sharing platforms herein may implement Internet Key Management Protocol (IKMP) to set up a secure tunnel between two peers. Moreover, data sharing platforms also preferably check the security policy of the data from the server and encrypts them when desired and/or suggested.

Secured virtual pipes may also be allocated for established secured sessions. According to different embodiments, the secured data flow may be classified based on IP addresses, Web Content, Application "Addresses", and/or other factors. In one approach, an administrator may configure different secured virtual pipes for different classes of data flow.

Security capabilities according to some embodiments may include encapsulating digital images (e.g., both still and motion) into encrypted IP packets that may be transported to the servers both locally and remotely. Such encrypted IP packets may implement IPsec DES, 3DES, AES 128, 192, 256 cryptology, etc. In other embodiments, security capabilities may include providing highly secure, virus free storage over Ethernet, WiFi and/or USB interfaces. As a result, such embodiments provide authentication and/or authorization, while using a 802.1x standard which, according to an illustrative approach, may include 802.1x EAP (TLS, TTLS, MD-5 and/or PEAP) at 128-bit or higher SSL.

ACLs may further restrict user access to applications, servers, and/or network management according to any of the embodiments described herein. It follows that a customer may be granted full control over the access to any applications or servers through the router. For network management functions, different privilege levels can be assigned to each user to restrict the available commands to configure the router.

However, for security reasons, the IP Network Address Translator (NAT) may be used to hide the internal IP address and port number from external clients. The preferred function of an exemplary NAT is to perform the translation between public IP addresses and private IP addresses. In different approaches, a NAT may involve either translating all internal IP addresses to one external IP address or mapping each internal IP address to one external IP address, either of which may be supported depending on the desired embodiment.

According to different embodiments, real time multimedia stream support may be handled by one or more of the following five protocols, e.g., by implementing a cloud network architecture.

A first protocol includes Real Time Streaming Protocol (RTSP). RTSP is an application-level protocol for controlling the delivery of real-time data over the Internet. In different approaches, RTSP may provide the framework to control the delivery of real-time data, such as audio and video, using Transmission Control Protocol (TCP) or the User Data Protocol (UDP).

Moreover, a second protocol includes Real Time Protocol (RTP). RTP is an UDP packet transport protocol that provides end-to-end network transport functions of real-time data, including audio and video. In various embodiments, RTP may provide the handling of timing reconstruction, loss detection, security, and/or content identification.

A third protocol includes Real Time Control Protocol (RTCP). In some approaches, RTCP may be appreciated as a companion protocol to RTP. RTCP may provide support for real-time conferencing of groups of any size within an Internet. In some embodiments RTCP includes support for source identification and support for gateways like audio and video bridges as well as multicast-to-unicast translators. Furthermore, RTCP may offer quality-of-service feedback from receivers to the multicast group as well as support for the synchronization of different media streams.

Furthermore, a fourth protocol includes Synchronized Multimedia Integration Language (SMIL) which preferably represents a layout language that allows easy creation of multimedia presentation consisting of multiple elements (e.g., including audio, video, text, images, graphics, etc.) in a common, synchronized data stream delivery.

The fifth protocol includes the Resource Reservation Protocol (RSVP). RSVP is used to reserve the necessary bandwidth for the real-time streaming data. RSVP may also be used to provide quality of service control. Within a given networking environment, the RSVP may be used to allow administrators to reserve and control the bandwidth for real-time streaming data paths.

Bandwidth reservation is essential for multimedia conferencing to guarantee a minimal level of uninterrupted service throughout the session. To avoid packetization overhead and/or delay, dedicated virtual channels may be allocated for real-time streaming data, including multimedia (e.g., video, audio, etc.). According to the present description, the virtual channels are preferably defined as "fixed rate" paths that have predictable quality and latency. Furthermore, many embodiments will support both unicast and multicast configurations. Thus, point to multi-point channels may be supported to allow for multimedia broadcasting capability.

According to an exemplary data sharing network, which is in no way intended to limit the invention, the data sharing platform may lie between RTSP servers and the Internet clients. Thus, the data sharing platform may detect and classify RTSP (e.g., streaming video and audio) traffic by inspecting the information that is exchanged between the RTSP servers and clients during the setup transaction. Moreover, it is preferred that the SEP also translates both the port numbers of the clients and the servers, in view of the fact that proxy functions may be performed by the data sharing platform. Thus, the data sharing platform may record the RTSP session information so that the TEARDOWN operations can be performed to the virtual channel for the RTSP sessions.

According to the various embodiments described herein, a data sharing platform may be scaled to embody any given size/scale. For example, in some embodiments, a data sharing platform may compute intensive engine in a cloud based Clinical Intelligent Micro Network (CIMN), while in others the data sharing platform may be scale down to a vital signs wearable or embedded device to an ASIC. However, it should be noted that although the physical size of the platform may change, telemedicine functionality does not.

It follows that, according to different in-use cases, the data sharing platform may be scaled to enable Healthcare as a Service (HaaS) for one in-use embodiment, while other in-use embodiments may focus on individual service, e.g., dynamically enable Ultrasound as a Service (Uaas), X-Ray as a Service (XaaS), Biometrics as a Service (BaaS), EEG/EKG as a Service (EAAS), EMR as a Service (EaaS), etc.

Figure 9:
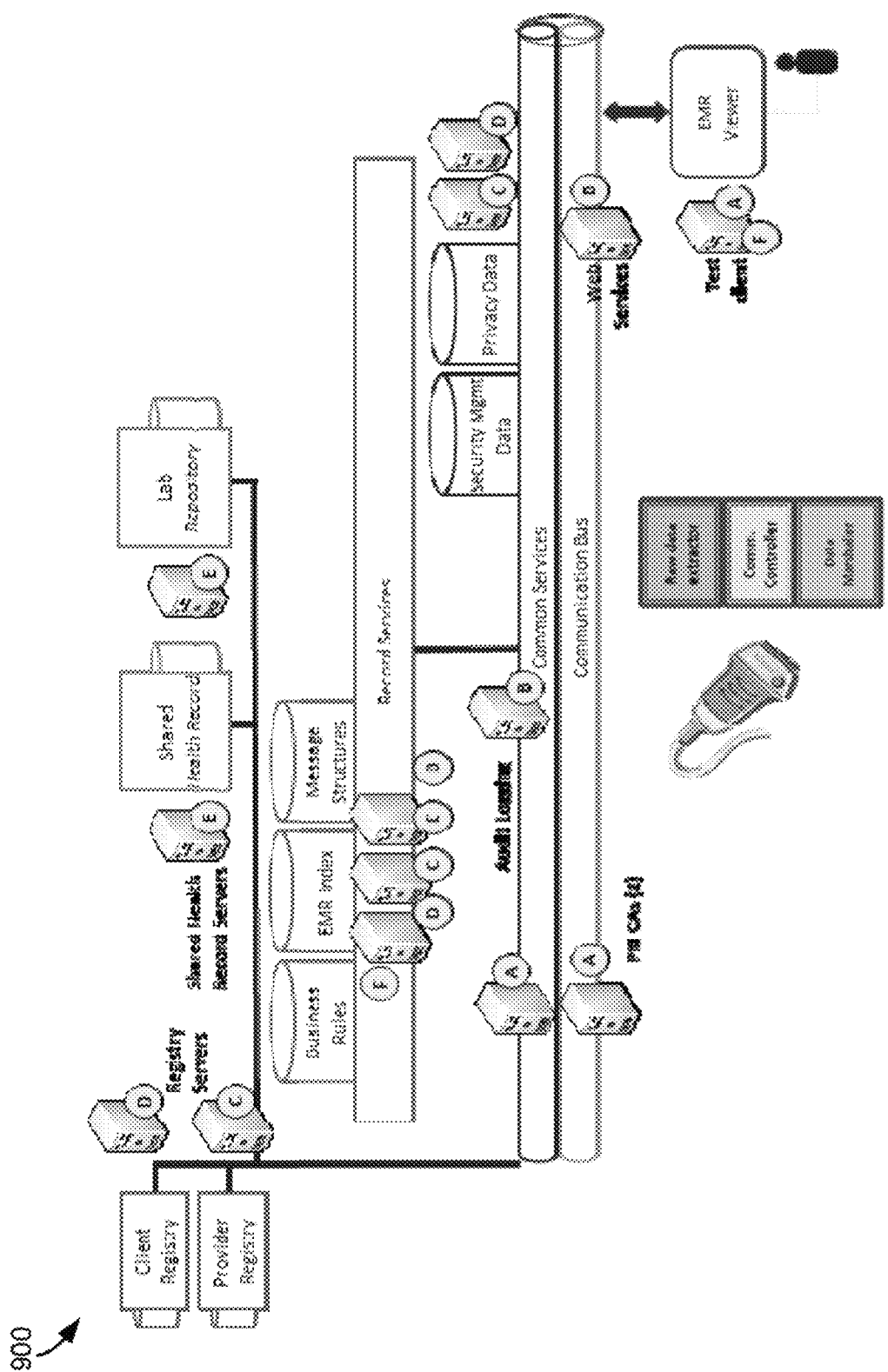
FIG. 9 is a data sharing platform having ultrasound as a service capability according to one embodiment.

FIG. 9 illustrates an exemplary data sharing platform 900 which enables UaaS using a cloud configuration according to an exemplary embodiment. As an option, the data sharing platform 900 may be implemented in conjunction with features from any other embodiment listed herein, such as those described with reference to the other FIGS. Of course, however, such data sharing platform 900 and others presented herein may be used in various applications and/or in permutations which may or may not be specifically described in the illustrative embodiments listed herein. Further, the data sharing platform 900 presented herein may be used in any desired environment. Thus FIG. 9 (and the other FIGS.) should be deemed to include any and all possible permutations.

According to the embodiment illustrated in FIG. 9, markers labeled "A"-"F" have been added to denote different features of the corresponding portion of the data sharing platform 900 as would be appreciated by one skilled in the art upon reading the present description. These markers are intended to denote the following features. "A" corresponds to authentication, "B" corresponds to submitting a transmission payload to the queue, "C" corresponds to establishing authorization, "D" corresponds to applying business rules, "E" corresponds to writing content to a repository, and "F" corresponds to exception handling.

Figure 10:
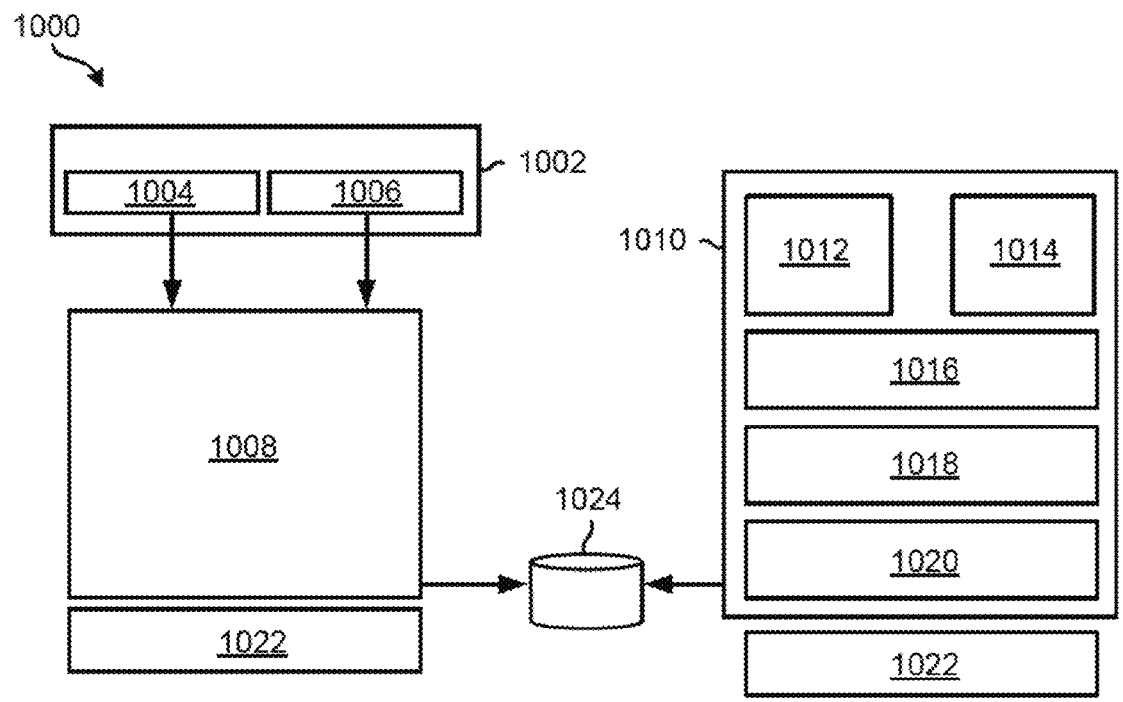
FIG. 10 is a delivery system according to one embodiment.

FIG. 10 illustrates an exemplary delivery system 1000 according to an exemplary embodiment. As an option, the delivery system 1000 may be implemented in conjunction with features from any other embodiment listed herein, such as those described with reference to the other FIGS. Of course, however, such delivery system 1000 and others presented herein may be used in various applications and/or in permutations which may or may not be specifically described in the illustrative embodiments listed herein. Further, the delivery system 1000 presented herein may be used in any desired environment. Thus FIG. 10 (and the other FIGS.) should be deemed to include any and all possible permutations.

Data sharing platforms as described herein are intended to be a software intensive platform. In other words, operating platforms associated with such data sharing platforms may nm on top of off-the-shelf platforms such as Windows, iOS, Android, etc. Looking to FIG. 10, the embodiment depicted therein illustrates an exemplary delivery system 1000 capable of producing data both securely and on-time. The delivery system of FIG. 10 has the capability to grab information from an enumerated set of medical devices EMRs and encapsulate them into packets for reliable transport, e.g., to a cloud network.

External system 1002 includes EMS 1004 and policy management 1006 which are both coupled to a control plane 1008 of a data sharing platform. Control plane 1008 may include EOC protocol stacks which, according to the desired implementation, may have capabilities and/or compatibilities including, but not limited to, WiFi, Ethernet, 4G. SNMP agent(s), policy manager(s), etc.

Referring still to FIG. 10, the delivery system 1000 further includes a data plane 1010 which may preferably provide active network implementation. Data plane 1010 includes internal and $3^{rd}$ party active applications 1012, 1014 respectively. Internal active applications 1012 may include any of the applications described and/or suggested herein such as firewall protection, video multicasting, App SLA, etc. Moreover, $3^{rd}$ party active applications 1014 may include programs that provide functionality in areas including billing, security, video conferencing, etc.

Data plane 1010 further includes EOS VM 1016, EOS node OS 1018 and processing devices 1020. According to different approaches, processing devices 1020 may include an enabled rout processor, enabled LTE processor, enabled policy enforcer, etc. Micro kernels 1022 are also incorporated with the delivery system 1000.

Furthermore, control plane 1008 and data plane 1010 are coupled to a database 1024 that may establish routes, develop WAN tags, establish policies, etc., or perform any other functions which would be apparent to one skilled in the art upon reading the present description.

The Image management Software may be downloadable from centralized server. Moreover, data may be stored in static and/or dynamic (as described above), Jpg. Bmp, tiff, etc. formats depending on the desired embodiment. Regardless of the storage format, data may be converted into DICOM format, e.g., for easy viewing on standard DICOM viewers at a server.

In further approaches, data may be integrated with external patient data management systems and/or may implement a customizable report format, as will soon become apparent.

As described above, data sharing platforms may be scaled to a desired size. For example, a data sharing platform may include compute intensive multi-core servers to Clinical Intelligent Micro Networks (CIMN) for telemedicine modems in one approach, while according to another approach, a data sharing platform may be scaled to wearable devices such as a telemedicine ASIC.

Figure 11A:
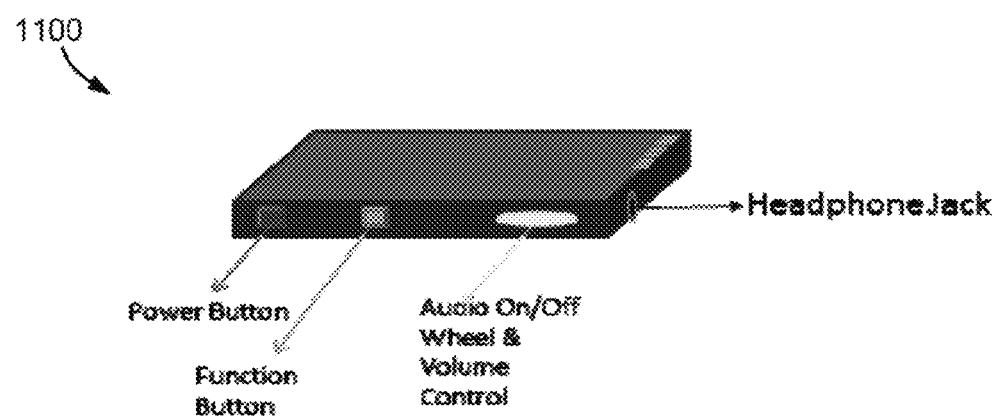
FIGS. 11A-11B are views from different angles of a data sharing platform configured as a telemedicine modem according to one embodiment.
Figure 11B:
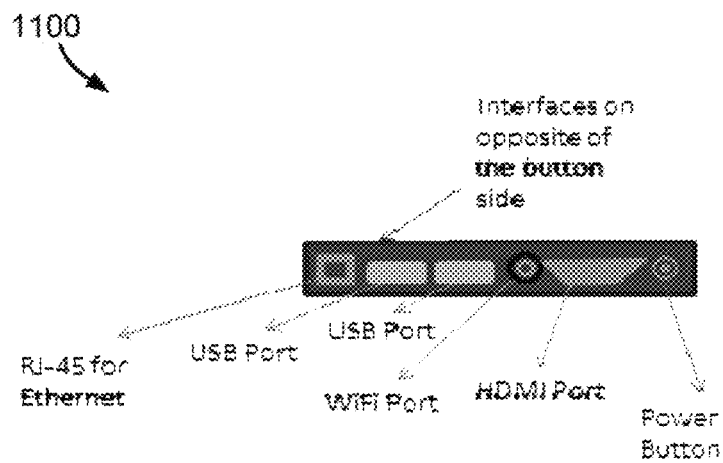
Figure 11C:
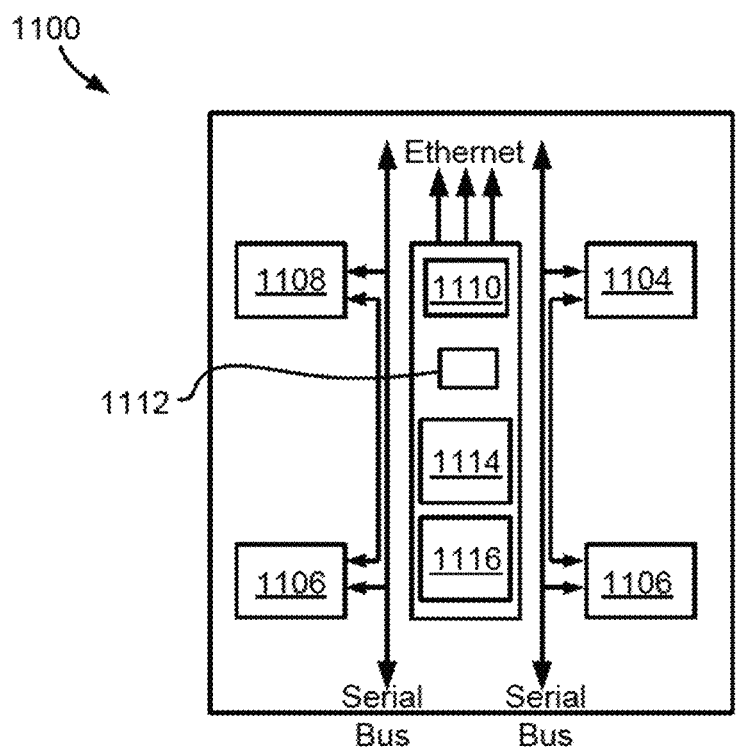
FIG. 11C is an internal circuit diagram of the data sharing platform in FIGS. 11A-11B.

FIGS. 11A-11C illustrate an exemplary data sharing platform 1100 according to an exemplary embodiment. As an option, the data sharing platform 1100 may be implemented in conjunction with features from any other embodiment listed herein, such as those described with reference to the other FIGS. Of course, however, such data sharing platform 1100 and others presented herein may be used in various applications and/or in permutations which may or may not be specifically described in the illustrative embodiments listed herein. Further, the data sharing platform 1100 presented herein may be used in any desired environment. Thus FIGS. 11A-11C (and the other FIGS.) should be deemed to include any and all possible permutations.

Looking to FIGS. 11A-11C, a data sharing platform configured as a telemedicine modem 1100 is illustrated according to one embodiment. FIG. 11A shows a perspective view of the modem 1100, while FIG. 11B depicts a side view. Moreover, FIG. 11C illustrates a circuit diagram of the components inside the outer casing of modem 1100 seen in FIGS. 11A-11B.

Looking specifically to FIG. 11C, the circuit diagram includes HDMI port, 1104, USB I/F components 1106, and 802.11 I/F component 1108. Furthermore, the circuit diagram includes Ethernet port 1110, CPU 1112, NMS layer engine 1114 (e.g., for layers 2-7) and security and image processing engine 1116. Any of the foregoing components of the circuit diagram may be constructed using conventional techniques and designs, and may be adapted for use in such embodiments, as would become apparent to one skilled in the art only upon reading the present description.

As an option, the present modem 1100 may be implemented in conjunction with features from any other embodiment listed herein, such as those described with reference to the other FIGS. Of course, however, such modem 1100 and others presented herein may be used in various applications and/or in permutations which may or may not be specifically described in the illustrative embodiments listed herein. Further, the modem 1100 presented herein may be used in any desired environment. Thus FIGS. 11A-11C (and the other FIGS.) should be deemed to include any and all possible permutations.

According to various different applications, the modem 1100 may be used as a back pack for the military, as a clinic/home healthcare controller, or any other application that would be apparent to one skilled in the art upon reading the present description. Moreover, in some approaches, the modem 1100 may be packaged for harsh environments like the mines, oil rigs, construction sites, etc. According to the present description, "packaged" is intended to mean that modem 1100 may be waterproofed, wrapped in a protective material, constructed of high strength material, or any other steps that may prevent damage and/or exposure of the internal components in the modem 1100.

According to some embodiments, a data sharing platform may be implemented as an ASIC as would be appreciated by one skilled in the art upon reading the present description.

Various embodiments herein have the capability of dynamically adjusting medical metrics for imaging, vital signs and waveforms. Furthermore, such embodiments have the inherent capability of self-learning and self-healing, and are thereby capable of providing improved reliability. According to further approaches having storage and data protection, load balancing, self-defending, intrusion prevention, virus eliminating expert systems, and other functions may be incorporated.

For embodiments having WAN, dynamic bandwidth allocation may be used to optimize high fidelity and high resolution multimedia connectivity. Furthermore, embodiments may provide self-tuning of the system, which may allow for dynamic changes to be made to the system, e.g., based upon the signal quality, without manual manipulation.

Some exemplary data sharing platforms may support one or more of support secure local and remote access, Telnet access for remote access, and/or multi-level password protected log-in with RADIUS authentication. According to an in-use embodiment, a minimum of five different levels of password protected access may be implemented. Accordingly, the highest of the five levels may be reserved for the Network Administrator who has total control over the node to, e.g., monitor, diagnose, configure, change, reboot, store, add, delete, remove, upload/download software, implement patches, etc. Moreover, a technician may have the second highest level of authority of the five levels, e.g., to configure, diagnose, monitor, reboot, etc. A third level of the five levels may be assigned to a user, thereby allowing the user the capability of monitoring and reading the status of the network. Furthermore, additional parties may be assigned different levels of the five level minimum.

A data sharing platform according to any of the embodiments described herein may have several levels of embedded QoS, SLAs and security functions (e.g., locking function for non-authorized users) for real time interaction, resiliency and industry strength for harsh environments. Illustrative examples, which are in no way intended to limit the invention, may include any of the following:

- 64 queues (input and/or output queues) with 8 priority levels. When a packet is received on a physical link, it is first put in a queue to be classified based on information in the packet (i.e. headers). This classification determines the input channel, e.g., including associated protocols.
- Processing to which the packet is directed. When tagging and priorities are set, it is put in an output queue for transport.
- Per flow queuing and customized priority queuing.
- Support for Random Early Detection (RED), which is described in IETF RFC-2309.
- Support for differentiated services.
- Support for Class Based Queuing (CBQ).
- Responsible identification means between platinum, gold and silver customers.
- Support for processing engine to calculate RTT for each session when establishing a session end to end.
- Support for processing engine to ensure critical RTT requirements such as real-time voice, video and data applications be met or exceeded.
- Engine allocation of 128 Mbytes buffer for priority queuing.
- Packet Classification, Forwarding, Queuing and/or Scheduling may be less than or equal to from about 2 ins to about 4 ms.
- Application Processor may support at least 3200MIPS (e.g., 60% utilization).

Moreover, various embodiments herein are preferably flexible and/or adjustable, and may thereby interface to any standard interface for LAN, WAN and/or SAN. For example, in telematics data sharing platforms may support one of more of the following. In one approach, a data sharing platform may send, receive and store information via telecommunication devices in conjunction with affecting control on remote objects. Moreover, in other approaches, a data sharing platform may include integrated use of telecommunications and informatics specifically caters for telemedicine vehicles, with may thereby allow for control of vehicles on the move.

Data sharing platforms as described herein may include an In-built Software Multipoint Control Unit (MCU). In one approach, the MCU may have simultaneous 16 multimedia sessions at a time. Accordingly, a server, e.g., in a cloud network, may have software that will provide video conferencing capability to each client.

Figure 12:
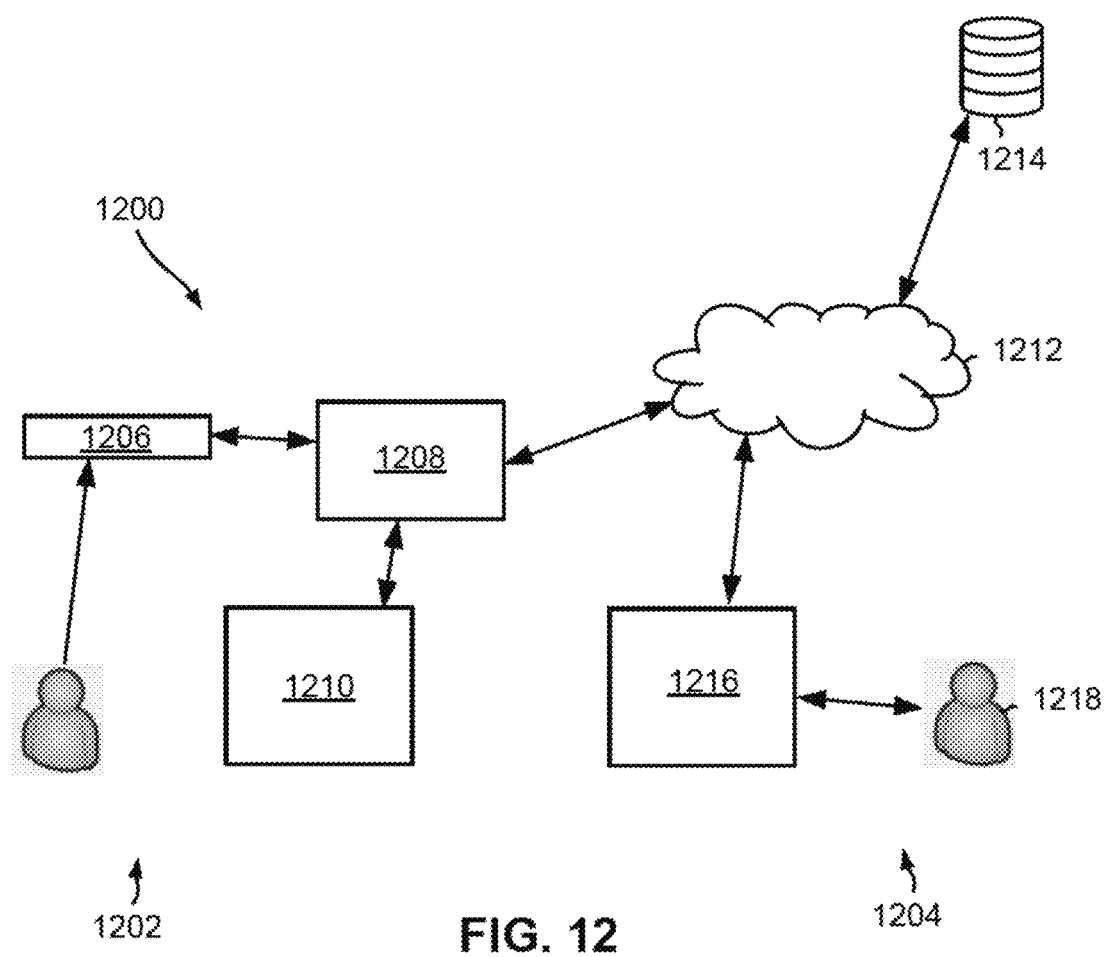
FIG. 12 is a data sharing platform according to one embodiment.

FIG. 12 illustrates an exemplary system 1200 according to an exemplary embodiment. As an option, the system 1200 may be implemented in conjunction with features from any other embodiment listed herein, such as those described with reference to the other FIGS. Of course, however, such system 1200 and others presented herein may be used in various applications and/or in permutations which may or may not be specifically described in the illustrative embodiments listed herein. Further, the system 1200 presented herein may be used in any desired environment. Thus FIG. 12 (and the other FIGS.) should be deemed to include any and all possible permutations.

Looking to FIG. 12, the embodiment illustrated therein includes a point to point connection between a local clinic at the first site 1202, and a radiologist at a remote site 1204. Moreover, although not illustrated in the embodiment of FIG. 12, a third client group may include a second radiologist at another remote site.

According to the present embodiment, the DVM at the local clinic at the first site 1202 may be conducting an ultrasound examination using a USB probe 1206 which is connected to a computing device 1208, e.g. a high resolution camera enabled laptop, desktop or tablet. The connectivity of the computing device 1208 may be made using any Wide Area Network (WAN) interface. It follows that three way video conferencing may be utilized in such an example. Moreover, it would be preferred if the three way video conferencing would incorporate industry standard protocols, as would be apparent to one skilled in the art upon reading the present description.

Computing device 1208 is further connected to display screen 1210 at the first site 1202, e.g. such that a technician may see the results of the exam being currently conducted on a patient. Computing device 1208 is also connected to cloud based computing environment 1212 which in turn is connected to back end storage database 1214.

Cloud based computing environment 1212 is also connected to display screen 1216 at the remote site 1204. Moreover, display screen 1216 is preferably a graphical user interface that may have different types of data shown in different unique regions of the display screen 1216 (graphical user interface). Furthermore, specialist 1218 at the remote location 1204 may input data through the display screen 1216 (graphical user interface), which may then be transmitted to the first site 1202, stored in the back end storage database 1214, stored in the cloud based computing environment 1212, etc.

It is desired that any of the embodiments described and/or suggested herein comply with various standards. Such standards may include, but are not necessarily limited to any one or more of the following: American Institute of Ultrasound in Medicine (AIUM), American Veterinary Medical Association (AVMA), Radiological Society of North America (RSNA), United States Department of Agriculture (USDA), Practice Management, American Telemedicine Association (ATA), American Medical Association (AMA), Food & Drug Administration (FDA), Health Insurance Portability and Accountability Act (HIPPA), Health Level 7 (HL-7) version 3.x, Continua Health Alliance, Patient Health Records, Digital Imaging and Communications in Medicine 3.0 (DICOM 3.0), Picture Archiving and Communications System (PACS), Technology Without An Interesting Name (TWAIN), IEEE 11073, Waveform. IEEE 802.1x, IEEE 802.3x, IEEE 802.11x, IEEE 802.15, TCP/IP, MPLS, SIP, VoIP, HTTP, XML, SNMP, RTP, RTSP, ARM, UDP, H.264, JPEG/MJPEG 2000. USB 2/3.0, HDMI, MIPI, RDBMS, NoSQL, TIA TR-069 for network management.

It is also preferred that any of the embodiments described and/or suggested herein are device agnostic. According to the present description, "device agnostic" is intended to mean that any of the embodiments described herein have the capability to use protocol conversion for an enumerated set of devices from known manufacturers and/or resellers. Moreover, any of the embodiments described and/or suggested herein may function over any operating system, e.g., Windows, IOS, Android, UNIX, etc.

The inventive concepts disclosed herein have been presented by way of example to illustrate the myriad features thereof in a plurality of illustrative scenarios, embodiments, and/or implementations. It should be appreciated that the concepts generally disclosed are to be considered as modular, and may be implemented in any combination, permutation, or synthesis thereof. In addition, any modification, alteration, or equivalent of the presently disclosed features, functions, and concepts that would be appreciated by a person having ordinary skill in the art upon reading the instant descriptions should also be considered within the scope of this disclosure.

Accordingly, one embodiment of the present invention includes all of the features disclosed herein, including those shown and described in conjunction with FIGS. 1A-12. Other embodiments include subsets of the features disclosed herein and/or shown and described in conjunction with FIGS. 1A-12. Such features, or subsets thereof, may be combined in any way using known techniques that would become apparent to one skilled in the art after reading the present description.

While various embodiments have been described above, it should be understood that they have been presented by way of example only, and not limitation. Thus, the breadth and scope of an embodiment of the present invention should not be limited by any of the above-described exemplary embodiments, but should be defined only in accordance with the following claims and their equivalents.

What is claimed is:

1. A method, comprising:
receiving a stream of biometric imaging data of a patient;
receiving medical data about the patient;
receiving a video stream depicting a source of the biometric imaging data;
receiving supplemental information selected from a group consisting of: a second video stream depicting a human, one or more use cases corresponding to the biometric imaging data, an image of anatomy comparable to the biometric imaging data;
preparing for simultaneous output to a graphical user interface on a single display screen: the biometric imaging data, the medical data about the patient, the video stream depicting a source of the biometric imaging data, and the supplemental information;
sending changes to the supplemental information to a remote server for saving said changes;
detecting, using a computer aided diagnostic program, and flagging a spot on an organ in the biometric imaging data; and automatically selecting an image of anatomy comparable to the biometric imaging data based on an analysis of the biometric imaging data without receiving user input, the selected image being sent to the second location; sending instructions to alter an acquisition characteristic of the biometric imaging data to a remote location, wherein the instructions are control instructions from a user, the instructions being for outputting to a device acquiring the biometric imaging data;

wherein each of the biometric imaging data, the medical data about the patient, the video stream depicting a source of the biometric imaging data, and the supplemental information is simultaneously output in a unique region of the graphical user interface, wherein the stream of biometric imaging data is received in real time concurrently with the video stream, and further comprising sending user input to a location of the source of the biometric imaging data, wherein the supplemental information includes the second video stream, wherein the second video stream is of a medical practitioner, wherein the medical practitioner also sees the information on the graphical user interface.

2. The method as recited in claim 1, wherein the biometric imaging data is ultrasound sonograph data.

3. The method as recited in claim 1, wherein the biometric imaging data is radiography data.

4. The method as recited in claim 1, wherein the biometric imaging data is compressed and transmitted at a rate of less than 800 kilobits per second.

5. A method, comprising:

receiving from a first location via a network a stream of biometric imaging data of a patient, wherein the biometric imaging data includes ultrasound sonograph data;

receiving medical data about the patient; receiving a video stream depicting a source of the biometric imaging data;

receiving supplemental information selected from a group consisting of: a second video stream depicting a human, one or more use cases corresponding to the biometric imaging data, an image of anatomy comparable to the biometric imaging data;

preparing for simultaneous output on a graphical user interface on a single display screen at a second location that is remote from the first location: the biometric imaging data, the medical data about the patient, the video stream depicting a source of the biometric imaging data, and the supplemental information;

sending the biometric imaging data, the medical data about the patient, the video stream depicting a source of the biometric imaging data, and the supplemental information to a device having the display screen at the second location; wherein each of the biometric imaging data, the medical data about the patient, the video stream depicting a source of the biometric imaging data, and the supplemental information is simultaneously output in a unique region of the graphical user interface;

receiving user input from the first location for controlling a device acquiring the ultrasound sonograph data;

sending the user input to the second location of the source of the biometric imaging data;

detecting, using a computer aided diagnostic program, and flagging a spot on an organ in the biometric imaging data; and automatically selecting the image of anatomy comparable to the biometric imaging data based on an analysis of the biometric imaging data without receiving user input, the selected image being sent to the second location; receiving instructions to alter an acquisition characteristic of the biometric imaging data from the remote location; and outputting the instructions to alter the acquisition characteristic of the biometric imaging data, wherein the instructions are control instructions from a user at the remote location, the instructions being output to a device acquiring the biometric imaging data; and sending changes to the supplemental information to a remote server for saving said changes, wherein the supplemental information includes the second video stream, wherein the second video stream is of a medical practitioner, wherein the medical practitioner also sees the information on the graphical user interface, wherein the stream of biometric imaging data is received in real time concurrently with the video stream, and further comprising sending user input to a location of the source of the biometric imaging data.

6. The method as recited in claim 5, wherein the biometric imaging data further includes radiography data.

* * * * *